(12) United States Patent
Huang et al.

(10) Patent No.: US 12,144,310 B2
(45) Date of Patent: Nov. 19, 2024

(54) TOBACCO PLANT RESISTANT TO SPOTTED WILT DISEASE WITHOUT LINKAGE DRAG AND METHOD FOR BREEDING THE SAME

(71) Applicant: Yunnan Academy of Tobacco Agricultural Sciences, Yunnan (CN)

(72) Inventors: Changjun Huang, Yunnan (CN); Yong Liu, Yunnan (CN); Haiqin Yu, Yunnan (CN)

(73) Assignee: Yunnan Academy of Tobacco Agricultural Sciences, Yunnan (CN)

( * ) Notice: Subject to any disclaimer, the term of this patent is extended or adjusted under 35 U.S.C. 154(b) by 0 days.

(21) Appl. No.: 17/763,779

(22) PCT Filed: Nov. 8, 2021

(86) PCT No.: PCT/CN2021/129382
§ 371 (c)(1),
(2) Date: Mar. 25, 2022

(87) PCT Pub. No.: WO2022/262179
PCT Pub. Date: Dec. 22, 2022

(65) Prior Publication Data
US 2024/0049674 A1    Feb. 15, 2024

(51) Int. Cl.
*A01H 6/82* (2018.01)
*A01H 1/00* (2006.01)
*A01H 1/02* (2006.01)
*A01H 1/04* (2006.01)
*C12Q 1/6895* (2018.01)

(52) U.S. Cl.
CPC ............... *A01H 6/823* (2018.05); *A01H 1/02* (2013.01); *A01H 1/045* (2021.01); *A01H 1/126* (2021.01); *C12Q 1/6895* (2013.01); *C12Q 2600/13* (2013.01)

(58) Field of Classification Search
None
See application file for complete search history.

(56) References Cited

FOREIGN PATENT DOCUMENTS

| CN | 110499389 A | * 11/2019 | ........... C12Q 1/6895 |
| WO | WO-2018119541 A1 | * 7/2018 | ................ C02F 3/34 |

OTHER PUBLICATIONS

Moon et al. (Crop Science, 47:1887-1894, 2007).*
Laskowska et al. (Euphytica, 193:207-219, 2013).*

* cited by examiner

*Primary Examiner* — Vinod Kumar
(74) *Attorney, Agent, or Firm* — Harness, Dickey & Pierce, P.L.C.; Anthony G. Fussner

(57) ABSTRACT

The invention relates to the field of tobacco breeding, particularly to a tobacco plant resistant to TSWD without linkage drag and a method for breeding the same. Provided is a tobacco plant or germplasm resistant to TSWD, which comprises a short RTSW introgressed segment, wherein at least part or entire of the sequence set forth in SEQ ID No.34 is deleted in the short RTSW introgressed segment as compared to the RTSW introgressed segment of tobacco 'Polalta'. Also provided is a method for screening said tobacco plant or germplasm, in which a tobacco plant or germplasm resistant to TSWD carrying a short RTSW introgressed segment is obtained by detecting NaChr4_2M, NaChr4_8M, NaChr3_62.6M and NaChr3_64.6M linkage drag locus markers. Compared with 'Polalta', the tobacco plant or germplasm provided by the invention not only has TSWD resistance, but also reduces or removes linkage drag.

10 Claims, 5 Drawing Sheets
Specification includes a Sequence Listing.

TOBACCO PLANT RESISTANT TO SPOTTED WILT DISEASE WITHOUT LINKAGE DRAG AND METHOD FOR BREEDING THE SAME

This patent application is a U.S. national stage filing under 35 U.S.C. § 371 of International Application No. PCT/CN2021/129382 filed Nov. 8, 2021. The disclosure of the application identified in this paragraph is incorporated herein by reference in its entirety.

FIELD OF THE INVENTION

The invention relates to the field of tobacco breeding, particularly to molecular markers for screening tobacco plants resistant to spotted wilt disease without linkage drag, tobacco plants resistant to spotted wilt disease without linkage drag, and methods for breeding the same.

BACKGROUND OF THE INVENTION

Tobacco spotted wilt disease (TSWD) is a severe disease caused by Orthotospoviruses infection. TSWD causes dwarfing of tobacco plants, wrinkled leaves, and small necrotic rings densely distributing on leaves. These rings often merge into large spots to form irregular necrotic areas. The disease expands rapidly from the infection site to the top of the tobacco plant. Apical buds of the plant wilt and droop, eventually leading to necrosis of the entire plant and completely losing economic value. Orthotospoviruses belong to family Tospoviridae in the order Bunyavirales, and Tomato spotted wilt virus (TSWV) is the type member of this genus. Orthotospoviruses has become a huge threat to agricultural production due to its wide host range and devastating economic losses. It is recognized as one of the most destructive viruses in plant viruses and ranks second in the list of the most important plant viruses in the world. Resistant to orthotospoviruses breeding is the most economical and effective approach for TSWD prevention and control, which also fundamentally meets the needs of agricultural green prevention and control. However, there are currently no flue-cured tobacco cultivars resistant to TSWD in cultivated tobacco (*Nicotiana tabacum* L.). All commercial tobacco cultivars are susceptible to TSWV and have been a potential threat to the epidemic and outbreak of TSWD.

Previous studies have shown that wild relatives possess many excellent alleles which can be utilized for crop varietal improvement. Discovering and effectively utilizing these desirable alleles from wild relatives, such as disease resistance genes, is conducive to enhancing disease resistance of cultivars, and has become one of the most indispensible methods for improving resistance of crops. Previous studies have shown that *Nicotiana alata*, a wild tobacco belonging to the genus *Nicotiana*, has good resistance to TSWV and is the only available germplasm of resistance to TSWD so far. *N alata* inoculated with TSWV only showed symptoms of hypersensitive necrosis on the inoculated leaves, and the presence of the virus was not detected in the systemic leaves. Using *N otophora* as a bridge parent, Gajos et al. successfully transferred the TSWV resistance locus (referred as RTSW locus, where RTSW is the abbreviation of Resistance to TSWV) from wild tobacco *N alata* to cultivated tobacco (*N tabacum* L.), and produced the variety 'Polalta' carrying a long RTSW introgressed segment. Genetic analysis of segregation population combined with molecular markers showed that RTSW was a single dominant locus, and few dominant molecular markers for RTSW locus were developed (Moon H, Nicholson J S, 2007. AFLP and SCAR Markers Linked to Tomato Spotted Wilt Virus Resistance in Tobacco. Crop Sci. 47, 1887-94.).

However, many genes unfavorable to agronomic traits often exist in wild relatives at the same time. If undesirable genes are closely linked to the target gene to be transferred, it will lead to linkage drag and increase the difficulty of utilizing desirable genes. Unfortunately, TSWD resistant tobacco 'Polalta' and other cultivated tobaccos carrying a long RTSW introgressed segment (including cultivated tobacco lines and varieties) all show severe linkage drag, mainly hampered by growth retardation, thickened veins, irregular distortions of veins, thickened leaves and veins, narrow leaves and other leaf deformations, dwarfing (FIG. 1), and varying degrees of reduced fertility, such as decreased seed setting rate, shriveled fruit and decreased seed quantity in a single fruit. Genetic linkage analysis indicates that the linkage drag may be derived from the linkage drag genes tightly linked to or co-segregated with the RTSW locus on the long RTSW introgressed segment, but the subtle genetic linkage relationship is still obscure. Global tobacco industry urgently needs TSWD resistance tobacco cultivars, but due to the existence of linkage drag, even though the RTSW locus has been introgressed to cultivated tobacco (*N tabacum* L.) for more than 40 years, there are not tobacco cultivars with high resistance to TSWD for commercial cultivation.

SUMMARY OF THE INVENTION

In order to address the above problems, the present invention provides molecular markers for identifying or screening cultivated tobacco (*N tabacum* L.) plants (including cultivated tobacco lines and varieties) resistant to TSWD without linkage drag and a method for breeding tobacco plants resistant to TSWD without linkage drag. Finally, by using the molecular markers and the method mentioned above, we obtained linkage drag-free TSWD resistance tobacco plants in this invention.

The invention discloses two linkage drag loci that lead to developmental deformations of leaves and plants in cultivated tobacco (including cultivated tobacco lines and varieties) with resistance to TSWD, wherein the first linkage drag locus (DEF1) comes from the end of chromosome 4 of *N alata*, which can be detected with the marker NaChr4_2M set forth in SEQ ID No. 10 and/or the marker NaChr4_8M set forth in SEQ ID No. 11; the second linkage drag locus (DEF2) comes from chromosome 3 of *N alata*, which can be detected with the marker NaChr3_62.6M set forth in SEQ ID No. 7 and/or the marker NaChr3_64.6 M set forth in SEQ ID No. 8. In order to obtain linkage drag-free TSWD resistance tobacco plants (including cultivated tobacco lines and varieties), both DEF1 and DEF2 loci need to be segregated separately or simultaneously from a plant carrying the RTSW locus.

The invention provides a method for detecting the linkage drag loci, DEF1 and DEF2. Specifically, the molecular markers NaChr4_2M (amplification primers are NaChr4_2MF/NaChr4_2MR) and NaChr4_8M (amplification primers are NaChr4_8MF/NaChr4_8MR) developed in the invention can be used to detect the DEF1 locus in backcross or self-cross segregation population. If the results of both primer pairs are negative, or the performances of the polymorphic markers with a genetic distance from the two markers within about 20 cM, 10 cM, 5 cM, 4 cM, 3 cM, 2 cM, 1 cM, 0.5 cM or less than 0.5 cM in a plant are consistent with that in the recipient parent, it indicates that the DEF1 locus has been segregated from the plant. Further, the molecular markers NaChr3_62.6M (amplification primers are NaChr3_62.6MF/NaChr3_62.6MR) and NaChr3_64.6 M (amplification primers are NaChr3_64.6MF/NaChr3_64.6MR) can be used to detect the DEF2 locus. If the results of both primer pairs are negative, or the performances of the polymorphic markers with a genetic distance from the two markers within about 20 cM, 10 cM, 5 cM, 4 cM, 3 cM, 2 cM, 1 cM, 0.5 cM or less than 0.5 cM in a plant are consistent with that in the recipient parent, it indicates that the DEF2 locus has been segregated from the plant.

The invention discloses a DNA segment having a nucleotide sequence set forth in SEQ ID No. 34. The segment is located on chromosome 3 of *N alata* and comprises the DEF2 locus. The DNA segment set forth in SEQ ID No. 34 is a non-target genomic segment closed to the RTSW gene (TSWD resistance gene) on the long RTSW introgressed segment in the tobacco material 'Polalta', and is a determinant of linkage drag in RTSW cultivated tobacco. Removal of part or entire of the sequence set forth in SEQ ID No. 34 from the long RTSW introgressed segment may reduce linkage drag. It will be understood by those skilled in the art that when removing part or entire of the sequence set forth in SEQ ID No. 34 from the long RTSW introgressed segment, simultaneously removing the upstream and downstream sequences at the 5' end and/or 3' end of the sequence set forth in SEQ ID No. 34 can also achieve the effect of reducing linkage drag.

The invention provides a tobacco plant or germplasm resistant to TSWD, which comprises a short RTSW introgressed segment without part or entire of the sequence set forth in SEQ ID No. 34, compared to a long RTSW introgressed segment of tobacco 'Polalta'.

In some embodiments of the invention, the tobacco plant or germplasm does not comprise a first linkage drag locus marker and/or a second linkage drag locus marker, wherein the first linkage drag locus marker comprises marker NaChr4_2M set forth in SEQ ID No. 10 and/or marker NaChr4_8 M set forth in SEQ ID No. 11, and the second linkage drag locus marker comprises marker NaChr3_62.6 M set forth in SEQ ID No. 7 and/or marker NaChr3_64.6 M set forth in SEQ ID No. 8; in particular, the marker NaChr3_62.6 M is located at 1-633 bp of the sequence set forth in SEQ ID No. 34; the marker NaChr3_64.6 M is located at 2210450-2210943 bp of the sequence set forth in SEQ ID No. 34.

In some embodiments of the invention, the second linkage drag locus marker further comprises NaChr3_44.2 M marker set forth in SEQ ID No. 1, NaChr3_54M marker set forth in SEQ ID No. 2, NaChr3_57M marker set forth in SEQ ID No. 3 and/or NaChr3_58M marker set forth in SEQ ID No. 4.

In some embodiments of the invention, the tobacco plant or germplasm comprises a TSWD resistance marker that comprises NaChr3_59 M marker set forth in SEQ ID No. 5.

In some embodiments of the invention, the tobacco plant or germplasm comprises NaChr3_59 M marker set forth in SEQ ID No. 5, and does not comprise NaChr4_2M marker set forth in SEQ ID No. 10, NaChr4_8 M marker set forth in SEQ ID No. 11, and NaChr3_64.6 M marker set forth in SEQ ID No. 8.

In some embodiments of the invention, the tobacco plant or germplasm comprises NaChr3_59 M marker, and does not comprise NaChr4_2M, NaChr4_8 M, NaChr3_44.2 M, NaChr3_58M or NaChr3_64.6 M marker.

In some embodiments of the invention, the tobacco plant or germplasm comprises NaChr3_59 M and NaChr3_62.6 M markers, and does not comprise NaChr4_2M, NaChr4_8 M, NaChr344.2M, NaChr3_54M, NaChr3_57M, NaChr3_58M, NaChr3_64.6M markers.

In some embodiments of the invention, the short RTSW introgressed segment is obtained by means of chromosome recombination, genome editing, chemical mutagenesis, physical mutagenesis, or artificial de novo gene synthesis.

In some embodiments of the invention, the tobacco plant or germplasm is selected from Burley tobacco, Dark tobacco, Flue-cured tobacco, Maryland tobacco, Oriental tobacco or Cigar tobacco.

In some embodiments of the invention, a novel TSWD resistance cultivated tobacco (*N tabacum* L.) plant is provided. The tobacco plant is resistant to TSWD caused by orthotospoviruses infection, and without any visible linkage drag. The novel tobacco plant comprises the RTSW locus conferring resistance to TSWD, but does not comprise the DEF1 and DEF2 loci. Specifically, in this plant, as compared with the known 'Polalta', the introgression segment derived from chromosome 4 of *N alata* is segregated (shown as negative for the molecular markers NaChr4_2M and NaChr4_8 M), and the 43-65 Mb segment of chromosome 3 of *N alata* is shortened, in particular, a segment derived from chromosome 3 of *N alata* is segregated, in particular, the results of the molecular marker test showed that NaChr344.2M, NaChr3_54M, NaChr3_57M, NaChr3_58M, NaChr3_62.6M and NaChr3_64.6 M are negative in this novel TSWD resistance tobacco.

The invention further provides a method for producing hybrid plant seeds using the novel TSWD resistance tobacco (*N tabacum* L.) plant provided by the invention. In a representative embodiment, the method comprises: using the novel TSWD resistance tobacco plant provided by the invention as the male parent or the female parent to form hybrid seeds with any tobacco (*N tabacum* L.) variety and line, and identifying, screening and producing cultivated tobacco (*N tabacum* L.) plants resistant to TSWD by the method of the invention.

The invention also provides a method for screening a tobacco plant or germplasm resistant to TSWD with reduced linkage drag, the method comprising:
  (a) screening tobacco plants or germplasms resistant to TSWD and isolating their nucleic acids;
  (b) detecting a first linkage drag locus marker and/or a second linkage drag locus marker in the isolated nucleic acids; the first linkage drag locus marker comprises NaChr4_2M marker set forth in SEQ ID No. 10 and/or NaChr4_8M marker set forth in SEQ ID No. 11; the second linkage drag locus marker comprises NaChr3_62.6 M marker set forth in SEQ ID No. 7 and/or NaChr3_64.6 M marker set forth in SEQ ID No. 8;
  (c) selecting a tobacco plant or germplasm resistant to TSWD that does not comprise the first linkage drag locus marker and/or the second linkage drag locus marker.

In some embodiments of the invention, NaChr4_2MF/NaChr4_2MR primer pair and NaChr4_8MF/NaChr4_8MR primer pair developed by the invention can be used to detect the molecular markers NaChr4_2M and NaChr4_8M in a tobacco backcross or self-cross population carrying the RTSW locus to screen a tobacco plant or germplasm resistant to TSWD with reduced linkage drag; If the detection results of both primer pairs are negative, or the performances of the polymorphic markers with a genetic distance from the two markers within about 20 cM, 10 cM, 5 cM, 4 cM, 3 cM, 2 cM, 1 cM, 0.5 cM or less than 0.5 cM in a tobacco plant are consistent with that in the recipient parent, it indicates that the DEF1 locus has been segregated from the tobacco plant. Further, NaChr3_62.6MF/NaChr3_62.6MR primer pair and NaChr3_64.6MF/NaChr3_64.6MR primer pair developed by the invention can be used to detect the molecular markers NaChr3_62.6 M and NaChr3_64.6 M to screen a tobacco plant or germplasm resistant to TSWD with reduced linkage drag; If the detection results of both primer pairs are negative, or the performances of the polymorphic markers with a genetic distance from the two markers within about 20 cM, 10 cM, 5 cM, 4 cM, 3 cM, 2 cM, 1 cM, 0.5 cM or less than 0.5 cM in a tobacco plant are consistent with that in the recipient parent, it indicates that the DEF2 locus has been segregated from the tobacco plant.

In some embodiments of the invention, the method for screening a tobacco plant or germplasm resistant to TSWD comprises: isolating nucleic acids of a tobacco plant or germplasm; detecting a TSWD resistance marker in the isolated nucleic acids; the TSWD resistance marker comprises NaChr3_59M marker set forth in SEQ ID No. 5; selecting a tobacco plant or germplasm comprising the TSWD resistance marker.

In some embodiments of the invention, the tobacco plant or germplasm resistant to TSWD is obtained by hybrid breeding methods, mutation breeding methods, genome editing breeding methods, and/or transgenic breeding methods.

In some embodiments of the invention, the second linkage drag locus marker further comprises NaChr3_44.2 M marker set forth in SEQ ID No. 1, NaChr3_54M marker set forth in SEQ ID No. 2, NaChr3_57M marker set forth in SEQ ID No. 3, and/or NaChr3_58M marker set forth in SEQ ID No. 4.

In some embodiments of the invention, the detection includes polymerase chain reaction or nucleic acid sequencing.

In some embodiments of the invention, the method for screening a tobacco plant or germplasm resistant to TSWD with reduced linkage drag comprises:
(a) crossing a RTSW locus-containing tobacco plant with a tobacco plant having rtsw/rtsw genotype to obtain a F1 tobacco plant having RTSW/rtsw genotype, and then backcrossing the F1 tobacco plant with a tobacco plant having rtsw/rtsw genotype to obtain a population material BC1F1 for screening a tobacco plant or germplasm resistant to TSWD with reduced linkage drag;
(b) isolating nucleic acids from BC1F1 tobacco plants, and using NaChr3_44.2 M primer pair, NaChr3_54M primer pair, NaChr3_57M primer pair, NaChr3_58M primer pair and NaChr3_59M primer pair respectively for PCR detection; screening tobacco plants detected as positive for NaChr3_59M primer pair, and negative for all of NaChr3_44.2 M primer pair, NaChr3_54M primer pair, NaChr3_57M primer pair and NaChr3_58M primer pair;
(c) testing TSWD resistance of the tobacco plants obtained in step (b);
(d) backcrossing the tobacco plants detected as positive for TSWD resistance in step (c) with a tobacco plant having rtsw/rtsw genotype to obtain a population material BC2F1; (e) observing the phenotype of the population material BC2F1 at the seedling stage, and pulling out plants with deformed development; among them, deformations in the seedling stage are mainly manifested as leaf deformations, including thickened veins, irregular distortions of veins, thickened leaves and veins, and narrow leaves; (0 testing the resistance of the plants with normal phenotype obtained in step (e) to TSWD, or extracting genomic DNA of the plants and then using NaChr3_59M primer pair for PCR detection, and screening a tobacco plant detected as positive for TSWD resistance test or positive for NaChr3_59M primer pair;
(g) isolating nucleic acids from the tobacco plants obtained in step (f), using NaChr4_2M primer pair, NaChr4_8 M primer pair, NaChr3_59M primer pair and NaChr3_64.6 M primer pair for genotyping; selecting a tobacco plant detected as positive for NaChr3_59M primer pair and negative for all of NaChr4_2M primer pair, NaChr4_8 M primer pair and NaChr3_64.6 M primer pair.

The population includes a population of BC1F1, BC2F1, BC3F1, BC4F1, BC5F1, BC5F2, BC5F3, BC6F1, BC6F2 . . . BCmFn obtained by crossing, backcrossing and self-crossing, where 'm' represents the number of generations of backcrossing, and 'n' represents the number of generations of self-crossing after backcrossing.

The invention also provides a method for breeding a tobacco plant or germplasm resistant to TSWD with reduced linkage drag, the method comprising:
(a) crossing a first tobacco plant or germplasm thereof with a second tobacco plant or germplasm thereof to produce a progeny tobacco plant or germplasm thereof, wherein the first tobacco plant or germplasm thereof comprises a TSWD resistance marker and does not comprise a first linkage drag locus marker and/or a second linkage drag locus marker; the TSWD resistance marker comprises NaChr3_59M marker set forth in SEQ ID No. 5; the first linkage drag locus marker comprises NaChr4_2M marker set forth in SEQ ID No. 10 and/or NaChr4_8 M marker set forth in SEQ ID No. 11; the second linkage drag locus marker comprises NaChr3_62.6M marker set forth in SEQ ID No. 7 and/or NaChr3_64.6 M marker set forth in SEQ ID No. 8;
(b) isolating nucleic acids from the progeny tobacco plant or germplasm thereof; (c) testing the TSWD resistance marker, the first linkage drag locus marker, and the second linkage drag locus marker in the isolated nucleic acids, thereby producing a progeny tobacco plant or germplasm that comprises the TSWD resistance marker and does not comprise the first linkage drag locus marker and/or the second linkage drag locus marker.

In some embodiments of the invention, the first tobacco plant or germplasm thereof is obtained by hybrid breeding methods, mutation breeding methods, genome editing breeding methods and/or transgenic breeding methods.

In some embodiments of the invention, the second linkage drag locus marker further comprises NaChr344.2M marker set forth in SEQ ID No. 1, NaChr3_54M marker set forth in SEQ ID No. 2, NaChr3_57M marker set forth in SEQ ID No. 3, and/or NaChr3_58M marker set forth in SEQ ID No. 4.

In some embodiments of the invention, the detection includes polymerase chain reaction or nucleic acid sequencing.

In some embodiments of the invention, the first tobacco plant or germplasm thereof and the second tobacco plant or germplasm thereof are selected from Burley tobacco, Dark tobacco, Flue-cured tobacco, Maryland tobacco, Oriental tobacco or Cigar tobacco.

The invention also provides a kit, comprising a primer set configured to detect a TSWD resistance marker, a first linkage drag locus marker, and a second linkage drag locus marker; the TSWD resistance marker comprises NaChr3_59M marker set forth in SEQ ID No. 5; the first linkage drag locus marker comprises NaChr4_2 M marker set forth in SEQ ID No. 10 and/or NaChr4_8 M marker set forth in SEQ ID No. 11; the second linkage drag locus marker comprises NaChr3_62.6 M marker set forth in SEQ ID No. 7 and/or NaChr3_64.6 M marker set forth in SEQ ID No. 8.

In some embodiments of the invention, the second linkage drag locus marker further comprises NaChr3_44.2 M marker set forth in SEQ ID No. 1, NaChr3_54M marker set forth in SEQ ID No. 2, NaChr3_57M marker set forth in SEQ ID No. 3, and/or NaChr3_58M marker set forth in SEQ ID No. 4.

In some embodiments of the invention, amplification primers of the NaChr3_59M marker are set forth in SEQ ID No. 20 and SEQ ID No. 21; amplification primers of the NaChr4_2 M marker are set forth in SEQ ID No. 30 and SEQ ID No. 31; amplification primers of the NaChr4_8 M marker are set forth in SEQ ID No. 32 and SEQ ID No. 33; amplification primers of the NaChr3_62.6 M marker are set forth in SEQ ID No. 24 and SEQ ID No. 25; amplification primers of the NaChr3_64.6 M marker are set forth in SEQ ID No. 26 and SEQ ID No. 27; amplification primers of the NaChr3_44.2 M marker are set forth in SEQ ID No. 12 and SEQ ID No. 13; amplification primers of the NaChr3_54M marker are set forth in SEQ ID No. 14 and SEQ ID No. 15; amplification primers of the NaChr3_57M marker are set forth in SEQ ID No. 16 and SEQ ID No. 17; amplification primers of the NaChr3_58M marker are set forth in SEQ ID No. 18 and SEQ ID No. 19.

The invention also provides a molecular marker set for screening a tobacco plant or germplasm resistant to TSWD with reduced linkage drag, which comprises a first linkage drag locus marker and/or a second linkage drag locus marker; the first linkage drag locus marker comprises NaChr4_2 M marker set forth in SEQ ID No. 10 and/or NaChr4_8 M marker set forth in SEQ ID No. 11; the second linkage drag locus marker comprises NaChr3_62.6 M marker set forth in SEQ ID No. 7 and/or NaChr3_64.6 M marker set forth in SEQ ID No. 8.

In some embodiments of the invention, the molecular marker set further comprises a TSWD resistance marker, the nucleotide sequence of which is set forth in SEQ ID No. 5.

The invention also provides a primer set for screening a tobacco plant or germplasm resistant to TSWD with reduced linkage drag, comprising: the primers set forth in SEQ ID No. 30 and SEQ ID No. 31 for amplifying NaChr4_2 M marker; the primers set forth in SEQ ID No. 32 and SEQ ID No. 33 for amplifying NaChr4_8 M marker; the primers set forth in SEQ ID No. 24 and SEQ ID No. 25 for amplifying NaChr3_62.6 M marker; the primers set forth in SEQ ID No. 26 and SEQ ID No. 27 for amplifying NaChr3_64.6 M marker; the primers set forth in SEQ ID No. 12 and SEQ ID No. 13 for amplifying NaChr344.2M marker; the primers set forth in SEQ ID No. 14 and SEQ ID No. 15 for amplifying NaChr3_54M marker; the primers set forth in SEQ ID No. 16 and SEQ ID No. 17 for amplifying NaChr3_57M marker; the primers set forth in SEQ ID No. 18 and SEQ ID No. 19 for amplifying NaChr3_58M marker.

In some embodiments of the invention, the primer set further comprises the primers set forth in SEQ ID No. 20 and SEQ ID No. 21 for amplifying NaChr3_59 M marker.

The invention also provides a method for screening a tobacco plant or germplasm resistant to TSWD, the method comprising: (a) isolating nucleic acids from a tobacco plant or germplasm; (b) testing at least one TSWD resistance marker in isolated nucleic acids; the TSWD resistance marker comprises NaChr3_59 M marker set forth in SEQ ID No. 5; (c) selecting a tobacco plant or germplasm comprising at least one TSWD resistance marker.

In some embodiments of the invention, the method comprises: (a) isolating nucleic acids from a tobacco line or variety to be tested; (b) detecting one or more markers tightly linked to the RTSW locus in isolated nucleic acids; and (c) based on the detection result of markers, selecting a tobacco plant with resistance to TSWD. Preferably, detecting NaChr3_59 M marker tightly linked to the RTSW locus in isolated nucleic acids; if the amplified product of NaChr3_59MF/NaChr3_59MR primer pair is positive, or the performances of the polymorphic markers with a genetic distance from the primer pair within about 20 cM, 10 cM, 5 cM, 4 cM, 3 cM, 2 cM, 1 cM, 0.5 cM or less than 0.5 cM in the tobacco line or variety are consistent with that in the donor parent 'Polalta', then it is a tobacco plant with resistance traits to TSWD.

In some embodiments of the invention, the detection includes polymerase chain reaction or nucleic acid sequencing.

In some embodiments of the invention, amplification primers of the NaChr3_59 M marker are set forth in SEQ ID No. 20 and SEQ ID No. 21.

The invention also provides a molecular marker for screening a tobacco plant or germplasm resistant to TSWD, the nucleotide sequence of which is set forth in SEQ ID No. 5.

The invention also provides molecular marker primers for screening a tobacco plant or germplasm resistant to TSWD, the nucleotide sequences of which are set forth in SEQ ID No. 20 and SEQ ID No. 21.

The invention also provides a method for introducing TSWD resistance into a tobacco variety, the method comprising: (a) crossing a tobacco donor parent (such as 'Polalta') having TSWD resistance with a tobacco recipient parent that does not have TSWD resistance to produce one or more progeny tobacco plants; (b) genotyping the one or more progeny tobacco plants, and detecting a polymorphic marker NaChr3_59 M linked to TSWD resistance; if the amplified product of NaChr3_59MF/NaChr3_59MR primer is positive, or the performances of the polymorphic markers with a genetic distance from the NaChr3_59M marker within about 20 cM, 10 cM, 5 cM, 4 cM, 3 cM, 2 cM, 1 cM, 0.5 cM or less than 0.5 cM in the progeny tobacco plant are consistent with that in the donor parent 'Polalta', then the progeny tobacco plant has resistance to TSWD; and (c) selecting progeny tobacco plants having resistance to TSWD. Preferably, the method further comprises backcrossing a selected progeny tobacco plant with a tobacco recurrent parent. The method further comprises: (d) crossing the selected progeny plant with itself or with the tobacco recurrent parent to produce one or more further progeny tobacco plants; and (e) selecting further progeny tobacco plants having resistance to TSWD. Preferably, the selection step (e) includes marker-assisted selection. Generally, the tobacco recipient parent is an elite cultivar. Generally, the genotyping step of these methods involves a determination of one or more molecular markers. Generally, the polymorphic markers used in the method include polymorphisms selected from the group consisting of single nucleotide polymorphisms (SNPs), insertions or deletions in DNA sequences (Indels), simple sequence repetitions of DNA sequences (SSR), restriction fragment length polymorphism (RFLP) and marker SNP.

The invention also provides tobacco plants and/or germplasms identified, produced or selected by the method of the invention, and any progeny or seeds derived from the tobacco plants or germplasms identified, produced or selected by the method.

Those skilled in the art should understand that the methods for obtaining TSWD resistant tobacco plants with reduced linkage drag, TSWD resistant tobacco plants with DEF1 and/or DEF2 loci segregated, and tobacco plants carrying a short RTSW introgressed segment include but are not limited to: hybrid breeding methods, chemical mutagenesis methods or physical mutagenesis methods, genome editing methods in biotechnology, and artificial de novo gene synthesis methods. Chemical mutagenesis methods include treatment with mutagens such as sodium azide, ethidium bromide, and ethyl methanesulfonate. Physical mutagenesis methods include treatment with X-rays, gamma rays, fast neutron radiation, heavy ion radiation and ultraviolet radiation. Genome editing methods in biotechnology include gene editing technologies such as CRISPR/Cas9 technology, zinc finger endonuclease (ZFN) technology, and transcription activator-like effector nuclease (TALEN). The method of removing DEF1 and/or DEF2 loci from the RTSW introgressed segment, or mutating DEF1 and/or DEF2 loci on the RTSW introgressed segment to make it lose its function also belongs to the protection scope of the invention.

Those skilled in the art should understand that the tobacco plants used in the method described herein can be Burley tobacco, Dark tobacco, Flue-cured tobacco, Maryland tobacco, Oriental tobacco or Cigar tobacco. The tobacco plants used in the method described herein are generally derived from common tobacco, and can be derived from multiple common tobacco varieties. The varieties include but are not limited to K326, Yunyan 87, Yunyan 97, Yunyan 85, Yunyan 116, Yunyan 121, NC 89, Zhongy an 100, Honghuadajinyuan, Cuibi No. 1, BU 64, CC 101, CC 200, CC 13, CC 27, CC 33, CC 35, CC 37, CC65, CC 67, CC 301, CC 400, CC 500, CC 600, CC 700, CC 800, CC 900, CC 1063, Coker 176, Coker 319, Coker 371Gold, Coker 48, CU 263, DF911, *Galpao* tobacco, GL 26H, GL 338, GL350, GL 395, GL 600, GL 737, GL 939, GL 973, GF 157, GF 318, RJR 901, HB 04P, K 149, K326, K 346, K 358, K394, K 399, K 730, NC 196, NC 37NF, NC 471, NC 55, NC 92, NC2326, NC95, NC 925, PVH 1118, PVH 1452, PVH 2110, PVH 2254, PVH 2275, VA116, VA119, KDH 959, KT200, KT204LC, KY 10, KY 14, KY 160, KY 17, KY 171, KY 907, KY907LC, KTY14×L8 LC, Little Crittenden, McNair 373, McNair 944, MsKY 14×L8, Narrow Leaf Madole, NC 100, NC 102, NC 2000, NC 291, NC 297, NC 299, NC 3, NC 4, NC 5, NC 6, NC7, NC 606, NC 71, NC72, NC 810, NC BH 129, NC 2002, Neal Smith Madole, OXFORD 207, ‘Perique’ tobacco, PVH03, PVH09, PVH19, PVH50, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN9OLC, TN 97, TN97LC, TN D94, TN D950, TR (Tom Rosson) Madole, VA 309, or VA359.

It is well known to those skilled in the art that in the primer sequence shown herein, 1-30 bases or any chemical modification can be added to the 5' end or 3' end respectively, wherein the added base type and chemical modification can be determined according to the base type of the matched region on the tobacco genomic DNA and the base pairing principle. The amplified product of the resulting primer pair is basically the same as that of the primer sequence shown herein (the DNA sequence between the forward primer and the reverse primer is the same). Therefore, the primer pairs obtained by adding 1-30 bases or any chemical modification at the 5' end or 3' end of the primer sequence shown herein and capable of amplifying substantially the same DNA segment are all included in the primer pairs of the invention. In a specific embodiment of the present invention, the primer pairs of the present invention are preferably the sequences set forth in SEQ ID No. 12-33.

Those skilled in the art should understand that examples of screening and selecting methods include, but are not limited to, Southern analysis, PCR amplification for detecting polynucleotides, Northern blotting, RNase protection, primer extension, RT-PCR amplification for detecting RNA transcripts, enzyme assays for detecting ribozyme activity of enzymes or polypeptides and polynucleotides, as well as protein gel electrophoresis, western blotting, immunoprecipitation, and enzyme-linked immunoassays for detecting polypeptides. Other techniques such as in situ hybridization, enzyme staining, and immunostaining can also be used to detect the presence or expression of polynucleotides. Methods of implementing all cited technologies are known.

Definition

Unless otherwise defined, all technical and scientific terms used herein have the same meaning as commonly understood by those of ordinary skill in the art to which the subject matter of this disclosure belongs. Although it is considered that the following terms can be well understood by those of ordinary skill in the art, the following definitions are proposed to make the subject of the present disclosure easy to understand.

The term “RTSW gene” refers to a gene in the genome of *N alata* that confers *N alata* resistance to TSWD.

The term “RTSW locus”, “RTSW resistance locus”, “TSWV resistance locus”, “TSWD resistance locus” or “TSWD resistance gene locus” refers to a DNA segment in the genome of *N alata* that contains the RTSW gene. This locus, in either heterozygous or homozygous state, confers tobacco plants resistance to TSWD.

The term “RTSW introgressed segment” or “resistance introgressed segment” refers to a DNA segment of *N alata* containing the RTSW gene. Generally, containing “RTSW introgressed segment” or “resistance introgressed segment” confers tobacco plants resistance to TSWD.

The term “short RTSW introgressed segment” or “short resistance introgressed segment” refers to a DNA segment that lacks part or all of non-target gene components (linkage drag gene components) linked to the RTSW gene on the long RTSW introgressed segment, and retains complete RTSW gene function.

The term “introgression” or “introgress” refers to the transfer of a desired allele of a genetic locus from one genetic background to another genetic background.

The term “linkage drag” refers to the linkage or co-segregation between favorable genes (target genes) and unfavorable genes (non-target genes) in a breeding process, so that when favorable genes are introgressed, unfavorable genes are also introgressed, often resulting in a new variety with undesirable traits. This kind of linkage drag is more common in the process of distant hybridization and backcross. The linkage drag of cultivated tobacco (*N tabacum* L.)

plants (including cultivated tobacco lines and varieties) resistant to TSWD herein is specifically manifested as varying degrees of developmental delay, dwarfing of plants, and leaf deformations including thickened veins, irregular distortions of veins, thickened leaves and veins, narrow leaves, etc., and varying degrees of reduced fertility, such as decreased seed setting rate, shriveled fruit and decreased seed quantity of a single fruit.

The term "linkage drag gene component" refers to a genomic component that contains a drag gene (non-target gene) but does not contain the RTSW gene (target gene) on a long RTSW introgressed segment. The "linkage drag gene component" can contain one or more "linkage drag loci". In a cultivated tobacco (N tabacum L.) plant resistant to TSWD, the "linkage drag gene component" is derived from the genome of N alata, specifically a segment derived from chromosome 4 of N alata, which can be detected with NaChr4_2M and NaChr4_8M molecular markers; and a shortened segment derived from chromosome 3 of N alata, which can be detected with NaChr344.2M, NaChr3_54M, NaChr3_57M, NaChr3_58M, NaChr3_62.6M and NaChr3_64.6M molecular markers.

The term "linked marker" refers to when a marker is linked to a trait and when the presence of the marker indicates whether and/or to what extent the desired trait or trait form will occur in the plant/germplasm comprising the marker, then the marker is "linked" to the trait. Similarly, when a marker is linked to an allele and when the presence of the marker indicates whether the allele is present in the plant/germplasm comprising the marker, then the marker is "linked" to the allele. For example, "a marker linked to TSWD resistance" refers to a marker whose presence or absence can be used to predict whether and/or to what extent a tobacco plant shows a TSWD resistance phenotype (for example, a marker linked to tobacco TSWD resistance, e.g. any molecular marker described in Tables 3, 5, and 7).

The term "TSWD resistance marker" refers to a DNA segment tightly linked to the RTSW gene (target gene) on the RTSW introgressed segment.

The term "linkage drag locus marker" refers to a DNA segment tightly linked to a drag gene (non-target gene) on the RTSW introgressed segment.

The term "trait" refers to one or more detectable characteristics of a cell or organism that can be affected by genotype. A phenotype can be observed with naked eyes, or by any other evaluation means known in the art, such as microscopy, biochemical analysis, genetic analysis, determination of tolerance to specific diseases, and the like. In some cases, a phenotype is directly controlled by a single gene or genetic locus, such as a "single gene trait". In other cases, a phenotype is a result of several genes.

The term "locus" is a region of a chromosome where a polymorphic nucleic acid, trait determinant, gene or marker is located. The locus contains one or more polymorphisms in the population; for example, there are alternative alleles in some individuals. The term "allele" refers to an alternative nucleic acid sequence at a specific locus. The length of the allele can be as small as one nucleotide base, but is usually larger. For example, the first allele appears on one chromosome, while the second allele appears on a second homologous chromosome. For example, alleles appear on different chromosomes of a heterozygous individual, or appear among different homozygous or heterozygous individuals in a population.

The term "chromosomal interval" refers to the continuous linear span of genomic DNA located on a single chromosome. The chromosomal region where the "locus" is located in this disclosure can also be replaced by "chromosomal interval". The term "chromosome" herein is also denoted as "Chr".

The term "centimole (cM)" is a unit of measurement of recombination frequency. One cM equals 1% probability that a locus will be separated from a target locus. The Kosambi function (Kosambi, The estimation of map distances from recombination values. Annals of Eugenics, 12:172-75 (1944)) can be used to calculate the genetic distance involved in this disclosure from the recombination value. As used herein, "tightly linked to" or "associated with" means that a marker or locus is within a genetic distance of about 20 cM, 10 cM, 5 cM, 1 cM, 0.5 cM or less than 0.5 cM from another marker or locus. For example, 20 cM means that the frequency of recombination between a marker and a locus is equal to or less than about 20%.

The term "genotype" refers to genetic composition of an individual (or individual group) at one or more genetic loci that are associated with observable and/or detectable and/or exhibited traits (phenotype). The genotype is defined by one or more alleles of one or more known loci that an individual has inherited from its parents. "Genotype" can be used to refer to genetic composition at a single locus or multiple loci, or more generally, the term "genotype" can be used to refer to individual genetic composition of all genes in its genome. It is possible, for example, to indirectly characterize a genotype using markers and/or directly characterize a genotype by nucleic acid sequencing.

The terms "backcross" and "backcrossed" refer to a method by which progeny plants are repeatedly backcrossed to one of their parents. In a backcross scheme, a "donor" parent refers to a parent plant that has a desired allele or locus to be introgressed. A "recipient" parent (used one or more times) or "recurrent" parent (used two or more times) refers to a parent plant into which a gene or locus is introgressed. An initial cross produces F1 generation. The term "BC1" refers to the second-use of a "recipient (recurrent)" parent, "BC2" refers to the third-use of a "recipient (recurrent)" parent, and so on. Specifically, in the present invention, the elite parent 'K326' is a "recipient (recurrent)" parent, and the breeding material 'Polalta' is a "donor" parent.

The results of using the tobacco plant breeding procedures described herein include the disclosed lines, cultivars, varieties, progenies, backcross lines, and hybrids. The terms "cultivar" and "variety" refer to a group of similar plants that can be distinguished from other varieties within the same species by structural or genetic characteristics and/or performance. Varieties are usually, although not always, sold commercially. Despite having one or more distinguishing traits, a further characteristic of a variety is that the overall differences between individuals within the variety are very small. It can be self-pollinated and selected for several generations, or asexually propagated from a single parent by tissue or cell culture techniques to produce "pure line" varieties. A variety can be essentially derived from another line or variety. According to the definition of International Convention for Protection of New Plant Varieties (established on 2 Dec. 1961, revised at Geneva on 10 Nov. 1972, 23 Oct. 1978, and 19 Mar. 1991), a variety "basically derived" from an initial variety, if: a) it is mainly derived from the initial variety, or from a variety mainly derived from the initial variety, while retaining the expression of the necessary characteristics resulting from the genotype or genotype combination of the initial variety; b) it is obviously different from the initial variety; c) except for the difference caused by the derivation behavior, it is consistent with the initial variety in the expression of the necessary characteristics resulting from the genotype or genotype combination of the initial variety. For example, a substantially derived variety can be obtained by selecting natural or induced mutants, somatic asexual mutations, mutated individuals derived from plants of the initial variety, backcrossing or transformation. Unlike varieties, "line" most often refers to a group of plants used for non-commercial use, such as for plant research. A line usually shows very small overall differences in one or more target traits between individuals, although there may be some differences in other traits between individuals.

The term "selecting" or "selection" refers to the behavior of choosing or picking desired individuals from a population based on certain predetermined criteria in the context of marker-assisted selection or breeding.

The term "elite line" or "elite variety" is a line with agronomic advantages, which is produced from a number of cycles of breeding for a certain superior agronomic performance. Numerous elite lines are available and are known to those of ordinary skill in tobacco breeding field. Similarly, "elite germplasm" or elite variety of germplasm is a germplasm with agronomic advantages. Specifically, it has advantages in many agronomic aspects such as germination rate, emergence rate, seed vigor, herbicide resistance, insect resistance, disease resistance; high yield; high grade index value; maturation property; maturation quality; mechanical harvest performance; maturity tolerance; leaf quality; height, plant maturity (e.g. early maturing, early maturing to middle maturing, middle maturing, middle-late maturing or late maturing); stem size (e.g. small, medium, or large stems); or the number of leaves per plant (e.g. few (e.g. 5-10), medium (e.g. 11-15), or many (e.g. 16-21) leaves) or any combination thereof.

The term "cell necrosis hypersensitive reaction" or "hypersensitive reaction" or "HR" is a typical disease resistance response of rapid cell necrosis that occurs after plant-pathogen incompatibility interaction, and is a disease resistance mechanism of plants, accompanied by programmed cell death. It is characterized by the burst of cellular reactive oxygen species, rapid response of related disease resistance marker genes, and local cell death.

The term "avirulence gene" or "avirulence gene NSm" means that according to the gene-to-gene hypothesis, for any host disease resistance gene, the pathogenic species has a corresponding avirulence gene. Only when a pathogen carrying an avirulence gene infects a host plant carrying a corresponding resistance gene, the plant will be induced to develop resistance, otherwise the plant will be infected and become diseased. In the invention, the avirulence gene NSm is specially prepared from TSWV-derived NSm protein, which can cause cell necrosis hypersensitive reaction (HR) in host plants carrying the resistance gene RTSW.

Avirulence gene-induced HR method can be used to detect TSWD resistance of tobacco. The method is disclosed in Chinese patent no. ZL201710414755.X that is titled "a method for identifying tobacco resistance using the tomato spotted wilt virus NSm gene", comprising steps of: (a) infiltrating a suspension of *Agrobacterium* carrying the avirulence gene NSm into the leave between veins of a tobacco test host, specifically comprising: culturing *Agrobacterium* carrying the avirulence gene NSm in *Agrobacterium tumefaciens* medium LB at 28° C. for 24 hours, collecting bacterial cells by centrifugation, and then diluting the bacterial cells with infiltration buffer to obtain a bacterial suspension with an OD600 of 0.5; using a sterile syringe with the needle removed to inject 9.5-10.5 microliters of the bacterial suspension from the leaf back of a tobacco plant into the leaf between veins to form a visible infiltration spot; placing the inoculated tobacco plant in an environment of 20-28° C. and 80% humidity, alternately providing continuous illumination for 16 hours and continuous darkness for 8 hours, and observing a total of 72 hours. (b) detecting the hypersensitive reaction of the test host, specifically comprising: using EHA105 strain carrying pK2-35S-NSm+ p2300-35S-Sw-5b as a positive control and EHA105 strain carrying pK2-35S-NSs as a negative control to perform the test on the tobacco host; observeing: if the tobacco test host shows hypersensitive reaction induced by the identified strain carrying the avirulence gene NSm expression vector, then the tested tobacco is identified as a tobacco plant with resistance to TSWD.

DESCRIPTION OF THE FIGURES

FIG. 1A shows the phenotype of leaf deformations, including thickened veins, irregular distortions of veins, thickened leaves and veins, and narrow leaves; FIGS. 1B and 1C show the deformed phenotypes of the whole plant, which are characterized by growth retardation, distortions of stems, and dwarfing of plants.

DESCRIPTION OF THE SEQUENCE LISTING

Figure 1:
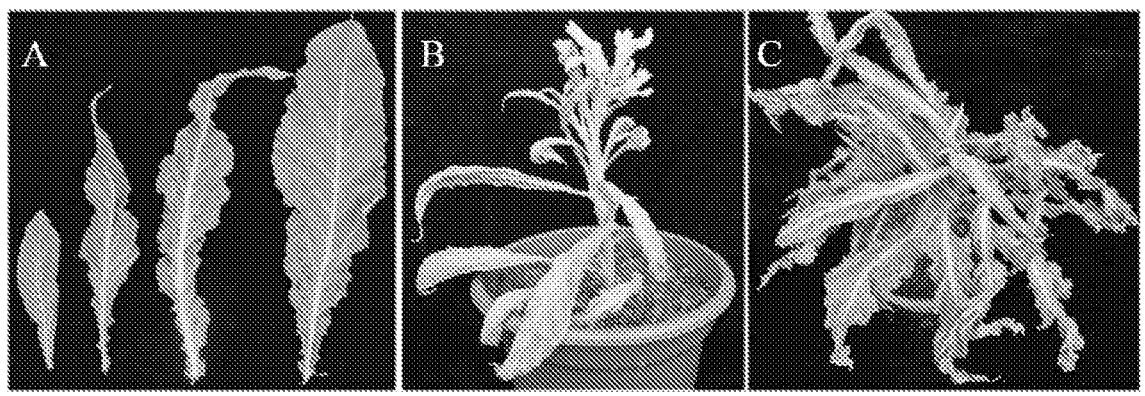
FIG. 1 shows the phenotype of linkage drag of tobacco plants carrying TSWD resistance locus. Tobacco plants were obtained by crossing the tobacco variety 'Polalta' as the donor parent and the susceptible elite cultivar '1(326' (*N tabacum* cv. K326) as the recipient parent, and backcrossing for 5 generations using '1(326' as the recurrent parent.

SEQ ID No. 1 is the nucleotide sequence of NaChr344.2M marker.
SEQ ID No. 2 is the nucleotide sequence of NaChr3_54 M marker.
SEQ ID No. 3 is the nucleotide sequence of NaChr3_57 M marker.
SEQ ID No. 4 is the nucleotide sequence of NaChr3_58 M marker.
SEQ ID No. 5 is the nucleotide sequence of NaChr3_59 M marker.
SEQ ID No. 6 is the nucleotide sequence of NaChr3_60 M marker.
SEQ ID No. 7 is the nucleotide sequence of NaChr3_62.6 M marker.
SEQ ID No. 8 is the nucleotide sequence of NaChr3_64.6 M marker.
SEQ ID No. 9 is the nucleotide sequence of NaChr3_65.7 M marker.
SEQ ID No. 10 is the nucleotide sequence of NaChr4_2M marker.
SEQ ID No. 11 is the nucleotide sequence of NaChr4_8M marker.
SEQ ID No. 12 is the forward primer used to amplify the NaChr344.2M marker.
SEQ ID No. 13 is the reverse primer used to amplify the NaChr344.2M marker.
SEQ ID No. 14 is the forward primer used to amplify the NaChr3_54 M marker.
SEQ ID No. 15 is the reverse primer used to amplify the NaChr3_54 M marker.
SEQ ID No. 16 is the forward primer used to amplify the NaChr3_57 M marker.
SEQ ID No. 17 is the reverse primer used to amplify the NaChr3_57 M marker.
SEQ ID No. 18 is the forward primer used to amplify the NaChr3_58 M marker.
SEQ ID No. 19 is the reverse primer used to amplify the NaChr3_58 M marker.
SEQ ID No. 20 is the forward primer used to amplify the NaChr3_59 M marker.
SEQ ID No. 21 is the reverse primer used to amplify the NaChr3_59 M marker.
SEQ ID No. 22 is the forward primer used to amplify the NaChr3_60 M marker.
SEQ ID No. 23 is the reverse primer used to amplify the NaChr3_60 M marker.
SEQ ID No. 24 is the forward primer used to amplify the NaChr3_62.6 M marker.
SEQ ID No. 25 is the reverse primer used to amplify the NaChr3_62.6 M marker.
SEQ ID No. 26 is the forward primer used to amplify the NaChr3_64.6 M marker.
SEQ ID No. 27 is the reverse primer used to amplify the NaChr3_64.6 M marker.
SEQ ID No. 28 is the forward primer used to amplify the NaChr3_65.7 M marker.
SEQ ID No. 29 is the reverse primer used to amplify the NaChr3_65.7 M marker.
SEQ ID No. 30 is the forward primer used to amplify the NaChr4_2M marker.
SEQ ID No. 31 is the reverse primer used to amplify the NaChr4_2M marker.
SEQ ID No. 32 is the forward primer used to amplify the NaChr4_8 M marker.
SEQ ID No. 33 is the reverse primer used to amplify the NaChr4_8 M marker.
SEQ ID No. 34 is a DNA sequence on the RTSW introgressed segment of 'Polalta' containing the second linkage drag locus (DEF2) but not the RTSW gene.

DETAILED DESCRIPTION OF THE INVENTION

The invention will be further described in detail below by examples. Those skilled in the art will understand that the following examples are only used to illustrate the invention and should not be regarded as limiting the scope of the invention. For those examples in which specific technologies or conditions are not indicated, it shall be carried out in accordance with the technologies or conditions described in the literature in the art or in accordance with the product specification. The reagents or instruments used without an indication of the manufacturer are all conventional products that can be obtained through purchase.

Tobacco material 'Polalta' is a TSWV resistant tobacco material carrying the RTSW locus (TSWD resistance locus), which has been published in a non-patent literature (Laskowska D, Berbeć A, 2010. TSWV resistance in DH lines of tobacco (N tabacum L.) obtained from a hybrid between 'Polalta' and 'Wiślica'. Plant Breeding 129, 731-3.). Tobacco variety '1(326' (N tabacum cv. K326) is a TSWV-susceptible tobacco material that does not possess the RTSW locus (TSWD resistance locus), which has been published in a non-patent literature (Edwards et al., 2017, A reference genome for Nicotiana tabacum enables map-based cloning of homologous loci implicated in nitrogen utilization efficiency. BMC Genomics 18, 448.), and the public can obtain its reference genome sequence from the website of solgenomics.net/organism/Nicotiana tabacum/genome. BC5F3, BC6F1 and BC6F2 progeny populations obtained by crossing of 'Polalta' and '1(326', backcrossing and self-crossing were created and preserved by our research group. N alata is a kind of wild tobacco resistant to TSWV, which has been published in a non-patent literature (Laskowska et al., 2013, A survey of Nicotiana germplasm for resistance to Tomato spotted wilt virus (TSWV). Euphytica 193, 207-19.). N alata used in the invention has an accession number of PI42334 in the tobacco germplasm bank of the United States. The above tobacco materials are common tobacco germplasm resources, and the public can obtain them from tobacco germplasm resources preservation organizations or Yunnan Academy of Tobacco Agricultural Sciences.

TSWV and *Agrobacterium* EHA105 carrying the avirulence gene NSm for resistance test are preserved in Yunnan Academy of Tobacco Agricultural Sciences. For the preparation method of *Agrobacterium* EHA105 carrying the avirulence gene NSm, see Chinese patent no. ZL201710414755.X, titled "A Method for Identifying Tobacco Resistance Using the Tomato Spotted Wilt Virus NSm Gene". The entire content of this patent is incorporated herein by reference.

Reagents: All molecular biology-related reagents, instruments and consumables are commercially available products.

Example 1. Acquisition of BC6F2 Segregation Population and Definition of TSWD Resistance with Linkage Drag The material 'Polalta' (5) carrying RTSW spotted wilt disease resistance locus was used as the donor parent to cross with the main susceptible variety '1(326' (?) (*N tabacum* cv. K326) as the recipient parent, and the progeny backcrossed with the recurrent parent 1(326' for 5 generations. Homozygous tobacco backcrossing and self-crossing generation BC5F3 was obtained by selecting disease resistance traits. After multiple generations of backcrossing, the resistance to TSWD was stable, but the deformed phenotypes still existed without any elimination. Deformed phenotypes included growth retardation, dwarfing of plants, and leaf deformations including thickened veins, irregular distortions of veins, thickened leaves and veins, narrow leaves, etc., as well as varying degrees of reduced fertility, such as decreased seed setting rate, shriveled fruit and decreased seed quantity of a single fruit (FIG. 1). The homozygous BC5F3 tobacco was used as the donor parent and the main susceptible variety 1(326' was used as the recurrent parent to continue backcrossing to obtain BC6F1 population, and BC6F1 population was self-crossed to obtain BC6F2 population. Using the avirulence gene induced HR method established by our team, 454 plants in the BC6F2 population were subjected to TSWD resistance identification. The avirulence gene induced HR method was the method for identifying tobacco resistance using the TSWV NSm gene that was recorded in the Chinese patent no. ZL201710414755.X, titled "A Method for Identifying Tobacco Resistance Using the Tomato Spotted Wilt Virus NSm Gene". The specific steps were as follows:

(1) culturing *Agrobacterium* EHA105 carrying the avirulence gene NSm expression vector in *Agrobacterium tumefaciens* medium LB at 28° C. for 24 hours, collecting bacterial cells by centrifugation, and then diluting the bacterial cells with infiltration buffer (10 mmol/L $MgCl_2$, 10 mmol/L MES, 200 μmol/L acetosyringone) to obtain a bacterial suspension with an $OD_{600}$ of 0.5;

(2) using a sterile syringe without needle to inject 9.5-10.5 microliters of the bacterial suspension between leaf veins from the leaf back of a tobacco plant to form a visible infiltration zone; inoculated tobacco plants were cultured with 20-28° C., 80% humidity and 16/8 light cycles for 72 hours.

(3) observing; if the tobacco plant showed typical hypersensitive reaction (HR) induced by the identified strain carrying the avirulence gene NSm expression vector, the tobacco plant was identified as a disease-resistant plant relative to the avirulent gene NSm.

By NSm mediated disease resistance identification, among the 454 plants of BC6F2 population, 319 plants showed HR phenotype and were resistant plants (indicated by RTSW), while 118 plants did not show HR phenotype and were susceptible plants (indicated by rtsw), and the other 17 plants were too small for HR test, so they were not included in the statistics.

Next, the genetic relationship of TSWD resistance locus was further verified using the HR test results. A chi-square test was performed on the resistance traits of the BC6F2 population. Under the premise that the expected ratio was 3:1, $\chi^2$=0.9344, when df=1, $\chi^2$0.05=0.3337, the test result $\chi^2$>0.3337, indicating it was not a significant difference. It was proved that the segregation of resistance traits in the BC6F2 population conformed to Mendel's law of inheritance. By chi-square test, it can be determined that RTSW gene-mediated resistance to TSWD is a single dominant gene (see Table 1 for the results).

TABLE 1

Segregation ratio of resistance traits in BC6F2 population

| Generation (Population) | HR (Resistant, RTSW) | No HR (Susceptible, rtsw) | Expected ratio | Chi-square value | Degree of freedom (df) | Progressive significance |
|---|---|---|---|---|---|---|
| BC6F2 | 319 | 118 | 3:1 | 0.9344 | 1 | 0.333722 |

Meanwhile, phenotype observation and statistical analysis of deformity was carried out. Based on the deformed phenotypes, the genetic relationship of the deformity locus was further verified. In the statistical process of deformed phenotypes, all abnormal leaves and plant development phenotypes were classified as deformed phenotypes and represented by DEF (Deformity), and phenotypes that plant development was completely normal without any deformations were classified as normal phenotypes and represented by def. A chi-square test was performed on the resistance traits of the BC6F2 population. The deformity (DEF): the normal (def) was 417:37=11.27:1, which was much higher than 3:1 and closer to a segregation ratio of 15:1. Under the premise that the expected ratio was 15:1, $\chi^2$=2.79, when df=1, $\chi^2_{0.05}$=0.094, the test result $\chi^2$>0.094, indicating that the difference was not significant. It was proved that the deformity traits in the BC6F2 population conformed to Mendel's law of inheritance, and was possibly determined by two loci.

The subpopulation BC6F2:S consisting of all susceptible plants in the BC6F2 population was also analyzed. There were 118 susceptible plants in the BC6F2:S population, and among them the deformity (DEF): the normal (def) was 81:37=2.18:1, which was closer to a segregation ratio of 3:1. Therefore, under the premise that the expected ratio was 3:1, $\chi^2$=2.54, when df=1, $\chi^2_{005}$=0.111, the test result $\chi^2$>0.111, indicating that the difference was not significant, and it was proved that the susceptible sub-population BC6F2: S conformed to Mendel's single-gene inheritance law (see Table 2 for the results).

TABLE 2

Segregation ratio of deformed phenotypes in BC6F2 population

| Generation (population) | Deformity | Normal | Expected ratio | Chi-square value | Degree of freedom (df) | Progressive significance |
|---|---|---|---|---|---|---|
| BC6F2 | 417 | 37 | 15:1 | 2.7964 | 1 | 0.094472 |
| BC6F2: S (susceptible) | 81 | 37 | 3:1 | 2.542 | 1 | 0.111 |

The results of phenotype analysis and chi-square test showed that the deformed phenotypes in the population were controlled by multiple genes, probably by two loci.

Figure 2:
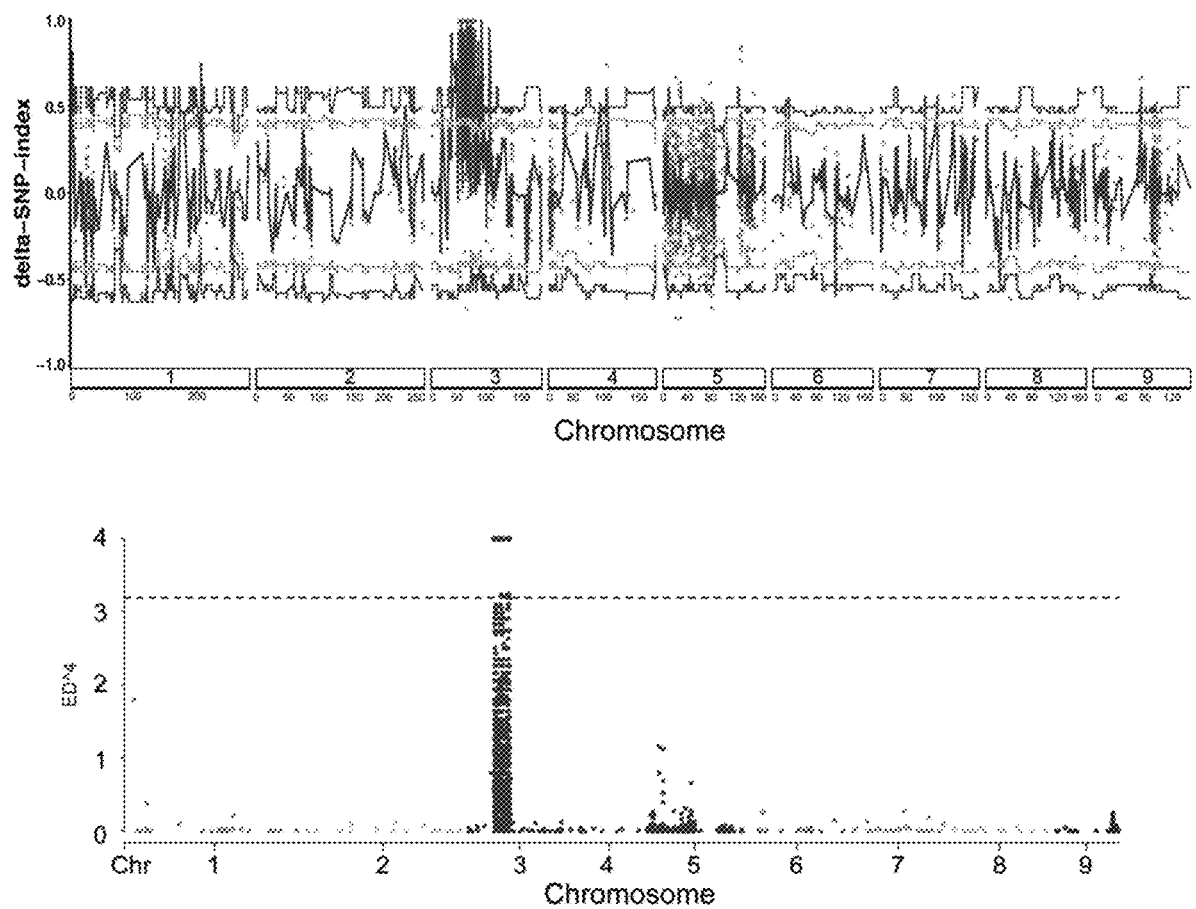
FIG. 2 shows the distribution of SNP sites between resistant pool (RTSW-pool) and susceptible pool (rtsw-pool) on chromosome 3 of *N alata* genome from 43.7 Mb to 64.8 Mb (Chr3: 43.7-64.8 Mb) that is found by analysis using algorithms of delta SNP-index and Euclidean distance (ED).

Example 2. Preliminary Localization of TSWD Resistance Locus and Molecular Marker Development In order to eliminate the interference of deformed phenotypes on localization of TSWD resistance locus, 40 deformed plants were randomly selected from 319 resistant plants to construct a resistant pool (RTSW-pool) and 40 deformed plants were randomly selected from 118 susceptible plants to construct a susceptible pool (rtsw-pool). 0.1 g leaves from each of the selected 40 plants were taken, and a total of 4 g leaves were mixed to form the RTSW-pool or rtsw-pool. The DNA of each pool was sequenced. The resistant parent 'Polalta' and the susceptible parent 'K326' were also sequenced. The sequencing depth was 30×, and 135G data was sequenced for each sample. Sequencing was performed using the BGI500 sequencing platform of BGI. The clean reads of the resistant pool and the susceptible pool obtained by whole genome sequencing were mapped to the chromosome level genome of Nalata respectively and analyzed by Bulked Segregant Analysis (BSA). Using delta SNP-index, a total of 7774 SNP sites between the resistant pool and the susceptible pool with a Delta value greater than 0.5 and a significance greater than 99% were found, of which 7732 SNP sites were distributed on chromosome 3 of the Nalata genome from 43.7 Mb to 64.8 Mb (Chr3: 43.7-64.8 Mb). The same result was also obtained by using Euclidean distance (ED) algorithm (see FIG. 2).

Example 3. Development and Verification of Molecular Markers of TSWD Resistance Locus According to the SNP distribution obtained from the BSA data of the resistant pool/susceptible pool, we believe that the resistance introgressed segment in the TSWD resistant tobacco in the BC6 population is derived from chromosome 3 of the Nalata genome from 43.7 Mb to 64.8 Mb, and its size is 21.1 Mb. In order to further decrease the size of the introgressed segment, molecular markers near the left end and the right end of the introgressed segment were developed (Table 3).

TABLE 3

Molecular markers of the resistance introgressed segment (1)

| Marker name | Primer name | Primer sequence (5'-3') | Position of the marker in the introgressed segment |
|---|---|---|---|
| NaChr3_44.2M | NaChr3_44.2MF | CTCTGCCTAGAT GTTGTTAATTGC (SEQ ID No. 12) | At the left end |
|  | NaChr3_44.2MR | GGATATGTCCGT AGATTTGGTTGA (SEQ ID No. 13) |  |
| NaChr3_64.6M | NaChr3_64.6MF | GCTGCTCAAACT GGCTTATGA (SEQ ID No. 26) | At the right end |
|  | NaChr3_64.6MR | CTAATAGATGCT CGTGACTTGTGA (SEQ ID No. 27) |  |
| NaChr3_65.7M | NaChr3_65.7MF | AGCATAAAGGTC GGAAGGAAGAAAGC (SEQ ID No. 28) | On the flank of the right end |
|  | NaChr3_65.7MR | TGACGGCTGATG ACGCATATCTCTA (SEQ ID No. 29) |  |

In order to verify the validity of the markers, N alata, TSWD resistant plant 'Polalta', TSWD susceptible variety '1(326', BC6F1 population and 437 plants of BC6F2 that have been identified as resistant or susceptible to TSWD were selected for marker verification. The method of marker verification was as follows: Leaf genomic DNA was extracted from a tobacco plant to be tested using Plant Genomic DNA Extraction Kit (TIANGEN Biotech, Cat. no. DP360) according to the operating steps described in the manual of the kit. For each marker, PCR amplification was performed using the leaf genomic DNA of the tobacco plant to be tested as a template and a primer pair consisting of two single-stranded DNA. The PCR reaction system was as follows: 2×Premix Ex TaqMix PCR Buffer (Takara, Cat. no. RR003A) 12.5 µL, 10 µmol/L forward primer 0.5 µL, 10 µmol/L reverse primer 0.5 µL, 50 ng/µL template DNA 1 µL, adding sterile double distilled water to a total volume of 25 µL. The PCR reaction procedure was as follows: pre-denaturation for 5 min at 94° C.; followed by 35 cycles: denaturation for 30 s at 94° C., annealing for 30 s at 55° C., extension for 30 s at 72° C. and a final elongation step for 10 min at 72° C. After reaction, the PCR product was identified by electrophoresis using ZAG DNA analyzer system (Agilent, M5320AA). If the expected PCR product was detected, the test result of the marker was positive; if the expected PCR product was not detected, the test result of the marker was negative. The above-mentioned method of marker verification is applicable to verification or detection of all the markers disclosed herein.

The results showed that NaChr3_65.7M marker was positive in N alata and 'Polalta', but negative in other tobacco plants 1(326', BC6F1 and BC6F2 populations. NaChr344.2M and NaChr3_64.6M markers were positive in tobacco 'Polalta', N alata, BC6F1 population and 319 BC6F2 tobacco plants resistant to TSWD, but negative in 1(326' and 118 susceptible BC6F2 tobacco plants. These markers are tightly linked to TSWD resistance, and co-segregate with TSWD resistance phenotype in each generation. Moreover, these markers are located at both ends of the resistance introgressed segment and can be used for the later detection of shortening of the resistance introgressed segment.

Example 4. Preliminary Localization of Linkage Drag Loci and Molecular Marker Development By resistance screening and deformed phenotype observation, the BC6F2 population can be preliminarily divided into three subpopulations: deformed resistant (genotype: DEF_RTSW), deformed susceptible (genotype: DEF_rtsw) and normal susceptible (genotype: def_rtsw). No plants with both normal phenotype and disease resistance (genotype: def RTSW) were found. 40 plants were selected from each of the three subpopulations to construct a deformed resistant pool (DEF_RTSW_pool), a deformed susceptible pool (DEF_rtsw_pool) and a normal susceptible pool (def_rtsw_pool) respectively. The construction method was taking 0.1 g leaves from each of the selected 40 plants, and mixing a total of 4 g to form a pool for DNA resequencing. The sequencing depth was 30×, and 135G data was sequenced for each pool.

Figure 3:
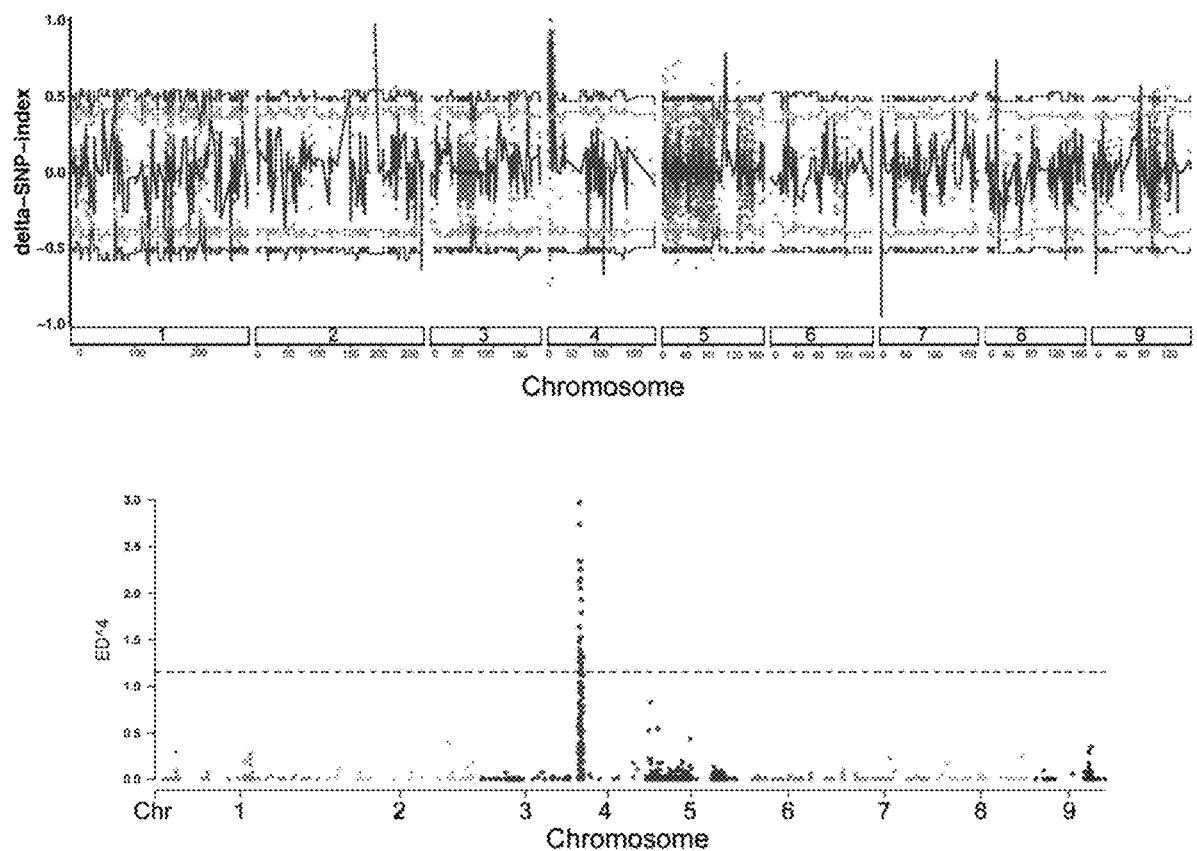
FIG. 3 shows the analysis results of deformed susceptible pool (DEF_rtsw_pool) and normal susceptible pool (def_rtsw_pool) using algorithms of delta SNP-index and Euclidean distance (ED). By Bulked Segregant Analysis (BSA), it was found that the DEF1 locus causing deformations was located at the end of chromosome 4 in the range of 1-8.6 Mb.

After the previous genetic analysis of the segregating population, it was preliminarily determined that the deformed phenotypes were determined by two dominant loci. For accurate localization of the first deformity locus (DEF1), the deformed susceptible pool (DEF_rtswpool) and the normal susceptible pool (def_rtswpool) were first selected for analysis to exclude the interference of the TSWD resistance locus. The whole genome sequencing data of the two pools and the parents was aligned to the genome of N alata, and delta SNP-Index and ED analysis was performed (FIG. 3). Through SNP typing, it was found that the deformity locus DEF1 was located in the range of 1-8.6 Mb at the end of chromosome 4 of the N alata genome. According to the whole genome sequencing results, two markers respectively near the left end and right end of the introgressed segment were developed (Table 4), which were located at 2 Mb and 8 Mb on chromosome 4 of the N alata genome.

TABLE 4

Molecular markers at both ends for the first deformity locus (DEF1) introgressed segment

| Marker name | Primer name | Primer sequence (5'-3') | Position of the marker in the introgressed segment |
|---|---|---|---|
| NaChr4_2M | NaChr4_2MF | TTGATGAC CTCGGTGA CCACTT (SEQ ID No. 30) | At the left end |
| | NaChr4_2MR | GGTCGATG AACTTGGC GTTGT (SEQ ID No. 31) | |
| NaChr4_8M | NaChr4_8MF | TGACTTCCA TATTGAGAA GCCGATTGA (SEQ ID No. 32) | At the right end |
| | NaChr4_8MR | GAGATCCGT CTGTACGAC TACCTGTA (SEQ ID No. 33) | |

Using these markers and combined with TSWD resistance identification, 'Polalta', N alata, '1(326', BC6F1, and 118 BC6F2 tobacco plants that were deformed susceptible (DEF_rtsw) and normal susceptible (def_rtsw) were selected for marker verification. The method of marker verification was the same as shown in Example 3.

The results showed that in N alata, 'Polalta', BC6F1 and 81 deformed susceptible (DEF_rtsw) BC6F2 tobacco plants, the test results of NaChr4_2M and NaChr4_8 M markers were positive, which were completely consistent with the deformed phenotype; and in 1(326' and 37 BC6F2 tobacco plants that were normal susceptible (def_rtsw), the test results of the markers were negative, which were consistent with the normal phenotype. The NaChr4_2M and NaChr4_8 M markers are located at both ends of the resistance introgressed segment and are completely linked to the DEF1 locus, so they can be used for the detection of the DEF1 locus.

Example 5. Determination of the Second Deformity Locus (DEF2)

In order to find the second deformity locus, the obtained molecular markers (NaChr4_2M and NaChr4_8 M) located at both ends of the first deformity locus (DEF1) introgressed segment were used to screen plants with deformed phenotypes, and tobacco plants that did not possess the DEF1 introgressed segment were selected. 40 plants were randomly selected from the tobacco plants that did not possess the DEF1 introgressed segment to form a mixed pool (DEF2 pool) for whole genome sequencing. BSA was performed on the obtained whole genome sequencing data and the completely normal mixed pool (def pool). Delta SNP-Index and ED analysis was performed. The clean reads of DEF2 pool and def pool obtained by whole genome sequencing were mapped to the *N. alata* genome, and it was found that the deformity locus DEF2 and the resistance locus (RTSW) were in the same region. Both DEF2 and RTSW loci were located on chromosome 3 of the Nalata genome from 43.7 Mb to 64.8 Mb, suggesting that the DEF2 locus and the RTSW locus overlapped. 319 deformed plants of the BC6F2 population that did not possess the first deformity locus (DEF1) were detected using the molecular markers at both ends of the resistance introgressed segment, and the marker detection results were completely consistent with the deformed phenotype, indicating that the DEF2 locus should be tightly linked to the RTSW locus and located near the RTSW locus.

Example 6. Screening of Plants with Short Resistance Introgressed Segment

Primers NaChr344.2MF/NaChr344.2MR of the marker at the left end of the resistance introgressed segment and primers NaChr3_64.6MF/NaChr3_64.6MR of the marker at the right end of the resistance introgressed segment were used for screening from a backcrossing population. The heterozygous (RTSW/rtsw) plant of BC5F2 (BC5F2-4Q) as donor parent was crossed with the recurrent parent 1(326' to produce BC6F1 backcross population. 1500 plants of the BC6F1 population were recruited for marker screening. If both markers are negative or positive, these plants were non-recombination individuals. If one marker is positive and another marker is negative, these plants were recombination events. For the primer pair NaChr344.2MF/NaChr344.2MR, the resistant control *N alata* and 'Polalta' generated a 470 bp amplified product, and the susceptible control 1(326' had no amplification, indicating that the PCR amplification was specific. The primer pair NaChr3_64.6MF/NaChr3_64.6MR was also used for amplification, the resistant control *N alata* and 'Polalta' obtained 494 bp amplified product, and the susceptible control 1(326' was negative, indicating that the PCR amplification was specific. DNA was extracted from leaves of 1500 plants of BC6F1 backcross population for PCR verification of markers. The method of marker verification was the same as that in Example 3. Finally, two plants (No. 46 and No. 364) were detected as negative for NaChr344.2M marker but positive for NaChr3_64.6 M marker, and one plant (No. 59) was detected as positive for NaChr344.2M marker but negative for NaChr3_64.6 M marker. By TSWD resistance identification (the method was the same as that in Example 1), we found that plant No. 59 was susceptible to TSWD as it did not show HR after inoculation with avirulence gene, meanwhile plants No. 46 and No. 364 showed HR after inoculation with avirulence gene. The results showed No. 46 and No. 364 plants were TSWD resistance plants, and they were preliminarily determined as plants with effective shortened resistance introgressed segment. In order to clarify the shortened size of the resistant introgressed segment in tobacco plants No. 46 and No. 364, more molecular markers were developed (Table 5).

TABLE 5

Molecular markers of resistance introgressed segment (2)

| Marker name | Primer name | Primer sequence |
|---|---|---|
| NaChr3_54M | NaChr3_54MF | GTGGAGGATACGA TTACGCCTGTC (SEQ ID No. 14) |
| | NaChr3_54MR | GCCATCATTAAC TGCTTGACCAAC C (SEQ ID No. 15) |
| NaChr3_57M | NaChr3_57MF | GGGTGTGTTTCG GGTTGTGAATCC (SEQ ID No. 16) |
| | NaChr3_57MR | CAGTTTCCGCTT CCACGGTTTGA (SEQ ID No. 17) |
| NaChr3_58M | NaChr3_58MF | GCACGCCGTCCA CTTTGAATG (SEQ ID No. 18) |
| | NaChr3_58MR | ACGAGGCTAGAC AGGACCTACAA (SEQ ID No. 19) |
| NaChr3_59M | NaChr3_59MF | GCATTGTTCCGA CTTGTAGAATCC TT (SEQ ID No. 20) |
| | NaChr3_59MR | GTGCCAATAGTTA CCACTGTTCCAA (SEQ ID No. 21) |

The size of the resistance introgressed segments carried by the plants No. 59, No. 46 and No. 364 were detected using these molecular markers, and the results were shown in Table 6.

TABLE 6

Test results of markers in recombination plants

| Individual plant | Marker name | | | | | | | Resistance identification |
|---|---|---|---|---|---|---|---|---|
| | NaChr3_44.2M | NaChr3_54M | NaChr3_57M | NaChr3_58M | NaChr3_59M | NaChr3_64.6M | NaChr3_65.7M | |
| 59# | Pos | Neg | Neg | Neg | Neg | Neg | Neg | No HR |
| 46# | Neg | Neg | Neg | Neg | Pos | Pos | Neg | Has HR |
| 364# | Neg | Neg | Neg | Pos | Pos | Pos | Neg | Has HR |

TABLE 6-continued

Test results of markers in recombination plants

| Individual plant | Marker name | | | | | | | Resistance identification |
|---|---|---|---|---|---|---|---|---|
| | NaChr3_44.2M | NaChr3_54M | NaChr3_57M | NaChr3_58M | NaChr3_59M | NaChr3_64.6M | NaChr3_65.7M | |
| *N. alata* | Pos | Pos | Pos | Pos | Pos | Pos | Pos | Has HR |
| 'Polalta' | Pos | Pos | Pos | Pos | Pos | Pos | Pos | Has HR |
| 'K326' | Neg | Neg | Neg | Neg | Neg | Neg | Neg | No HR |

Note:
"59#", "46#" and "364#" in the table represent "plant No. 59", "plant No. 46" and "plant No. 364" respectively. "Pos" means positive, "Neg" means negative, and "HR" means hypersensitive reaction. "Has HR" means having TSWD resistance, and "No HR" means not having TSWD resistance.

From Table 6, we found that plant No. 46 contains a shorter resistance introgressed segment. NaChr344.2M, NaChr3_54M, NaChr3_57M, and NaChr3_58M are negative in plant No. 46. It means the introgressed segment has been shortened by more than 14 Mb in plant No. 46. By resistance identification, it was speculated that the resistance gene locus should locate between 58 Mb and 64.8 Mb on Chr3 of the *N alata* genome.

The molecular markers (NaChr4_2M and NaChr4_8M) located at both ends of the first deformity locus (DEF1) introgressed segment were used to detect plant No. 46 and the result was positive. Since plant No. 46 carried the DEF1 locus, it still had a severe deformed phenotype. Our results indicated that the DEF1 locus and RTSW (DEF2) locus were located on different chromosomes and should be segregated separately. Therefore, we tried to screen plants carrying only the RTSW (DEF2) introgressed segment among the progenies of plant No. 46. 248 plants of F2 self-crossing segregating population of plant No. 46 were subjected to screening, and a total of 60 plants carrying only the RTSW (DEF2) locus but no DEF1 locus were obtained. However, all of these 60 plants still showed severe deformed phenotypes. Among them, 34 plants were unable to bloom at all, and other 26 plants were delayed in flowering and few-flowered. Among them, 4 plants had only 1-2 flowers with low seed setting rate and seed quantity.

Example 7. Genetic Relationship of Linkage Drag Loci

Figure 4:
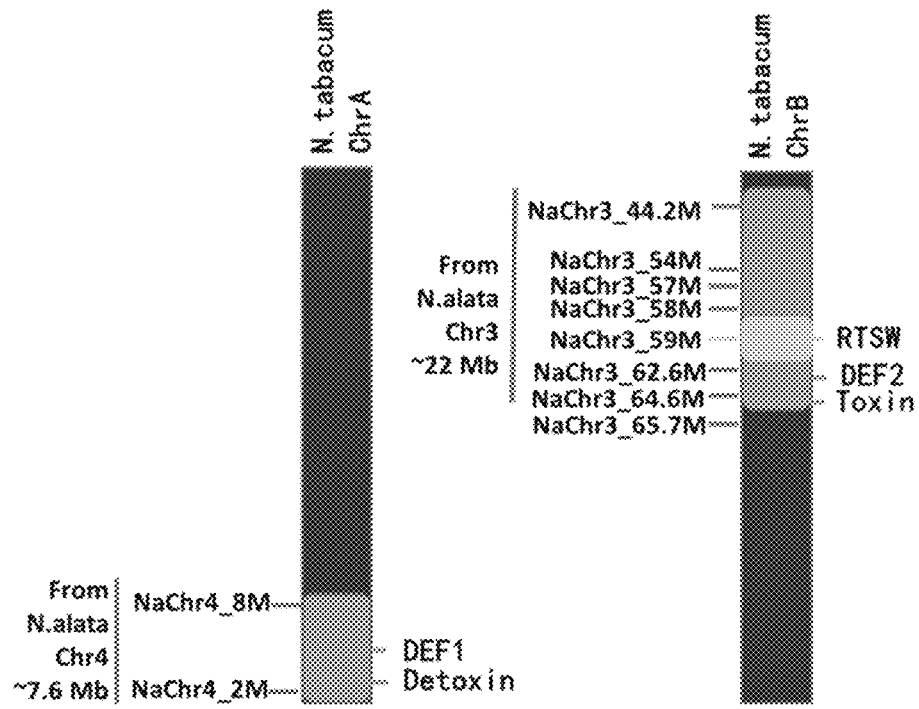
FIG. 4 shows the predicted genetic models of DEF1 and RTSW (DEF2) loci. DEF1 locus is derived from 1-8.6 Mb of chromosome 4 of wild tobacco *N alata*. DEF2 locus is tightly linked to the resistance locus (RTSW locus). They are located at the same locus that is derived from 43.7 Mb to 64.8 Mb of chromosome 3 of *N alata*. It is speculated that there may be a tightly linked toxin gene (Toxin) near the RTSW (DEF2) locus, and the existence of RTSW (DEF2) locus alone may lead to heavier deformed phenotype or impaired fertility, while DEF1 locus may be tightly linked to a detoxin gene (Detoxin), and only in the presence of DEF1 locus, RTSW (DEF2) locus can be inherited stably. The markers used in the invention have been marked in the figure.

According to the analysis of the disease resistance locus (RTSW) and the deformity loci (DEF), the genetic relationship between the RTSW locus and DEF loci was preliminarily revealed. We found that the deformed phenotype was determined by two loci. DEF1 was derived from 1-8.6 Mb on chromosome 4 of the genome of the wild tobacco *N alata*. The other locus (DEF2) was tightly linked to the resistance locus (RTSW) and located on the same genome region, 43.7 Mb to 64.8 Mb, of *N alata* Chr3. In the continuous backcrossing process of multiple generations, the DEF1 locus and RTSW (DEF2) locus showed co-segregation all the time. Through investigation of the F2 segregated population of plant No. 46, we speculate that the DEF1 locus is essential for the surviving of RTSW (DEF2) locus. If there is only RTSW (DEF2) locus, plants will show more severe deformity and poor fertility. If DEF1 and RTSW (DEF2) loci co-exist, plants will show severe deformed phenotypes, but the fertility is not significantly different from that of the parents 'Polalta' and 1(326'. Therefore, we proposed the following model: there may be a toxin gene (Toxin) near the RTSW (DEF2) locus, which alone may cause a more severe deformed phenotype and sterility, while there may be a detoxin gene (Detoxin) at the DEF1 locus. The RTSW (DEF2) locus can be stably inherited only in the presence of the DEF1 locus (FIG. 4).

Example 8. Simultaneous Removal of Two Linkage Drag Loci by Screening from a Super Large Population According to our model, there may be a toxin gene near the RTSW (DEF2) locus, which alone may cause a more severe deformed phenotype and sterility, while there may be a detoxin gene at the DEF1 locus, and the RTSW (DEF2) locus can be inherited stably only in the presence of the DEF1 locus. Therefore, in order to segregate the DEF1 locus, it is necessary to segregate the gene segment that causes sterility at the RTSW (DEF2) locus simultaneously. In order to obtain a completely normal plant, the DEF2 locus must also be segregated. However, the introgressed segments of DEF1 and RTSW (DEF2) derived from wild tobacco *N alata* have low homology with the sequence in cultivated tobacco, so recombination inhibition will occur, resulting in a low recombination rate. In order to shorten the introgressed segments of DEF1 and RTSW (DEF2) simultaneously and obtain completely normal resistant plants, it is necessary to screen a huge segregation population. Deformed phenotypes can be used as the visible marker for screening at the seedling stage. For phenotypic screening, the BC7F1 backcross population was produced by using plant No. 46 as the male parent (RTSW(DEF2)/rtsw(def2), DEF1/def1 genotype) and 1(326' as the female parent, and were seeded in the seedling pond, with 1600 floating plates, about 100 seeds per plate. A total of more than 160,000 seedlings were subjected to screening. During the seedling stage, for deformed phenotypes, a total of 5 rounds of screening were carried out. Once the deformed seedlings were observed, they would be discarded during the screening. After critical screening, 12,000 completely normal seedlings were finally obtained for the next molecular marker screening.

Figure 5:
FIG. 5 shows part of the results of screening using molecular markers NaChr3_59M and NaChr3_64.6 M located at both ends of the resistance introgressed segment of plant No. 46. Molecular markers at both ends of the RTSW (DEF2) locus were used simultaneously to screen. Using an optimized molecular marker screening system, 18 plants comprising at least one of the molecular markers NaChr3_59M and NaChr3_64.6 M were obtained.

Genomic DNA was extracted from the 12,000 tobacco plants for marker screening. First, molecular markers NaChr3_59M and NaChr3_64.6M located at both ends of the resistance introgressed segment of plant No. 46 were simultaneously used for screening. Using our optimized molecular marker screening system, 18 plants with at least one of the markers (NaChr3_59M and NaChr3_64.6M) positive were obtained (FIG. 5).

Next, the 18 plants were further tested using the markers at the DEF1 locus (NaChr4_2M and NaChr4_8M). All the plants were negative for primer pairs NaChr4_2MF/NaChr4_2MR and NaChr4_8MF/NaChr4_8MR, indicating that all the plants do not contain the DEF1 locus.

These 18 plants were then submitted to identify the resistance property to TSWD by using avirulence gene mediated HR (described in Example 1). By transiently expressing the avirulent gene NSm and observing the HR response, it can be determined whether there is a resistance introgressed segment. Finally, 5 plants that could be induced HR response when the avirulent gene was expressed were screened out of the 18 plants. The 5 plants have TSWD resistance, named as plant No. 1, plant No. 4, plant No. 11, plant No. 12, and plant No. 17.

In order to detect the size of the resistance introgressed segment carried by the 5 plants and select the shortest resistance introgressed segment for future breeding program, more molecular marker detection on the 5 selected resistant plants were carried out. Using the sequence of the genome, two new pairs of molecular marker primers were further developed for detection based on the resistance introgressed segment (Table 7).

TABLE 7

Molecular markers of the resistance introgressed segment (3)

| Marker name | Primer name | Primer sequence (5'-3') |
|---|---|---|
| NaChr3_60M | NaChr3_60MF | TCTTACCTCTCCT ACTACTCCTCCAT C (SEQ ID No. 22) |
|  | NaChr3_60MR | GCATCTTCTTCTTC TCCGTATCTCCAA (SEQ ID No. 23) |
| NaChr3_62.6M | NaChr3_62.6MF | CTTAGCAGGCAACC AGACAG (SEQ ID No. 24) |
|  | NaChr3_62.6MR | GAGAATGAGCAAGA GAATGTGTTAG (SEQ ID No. 25) |

It was found that plant No. 12 carried the shortest resistance introgressed segment. Plant No. 12 was only positive for NaChr3_59M marker, but negative for other markers (Table 8).

Figure 6:
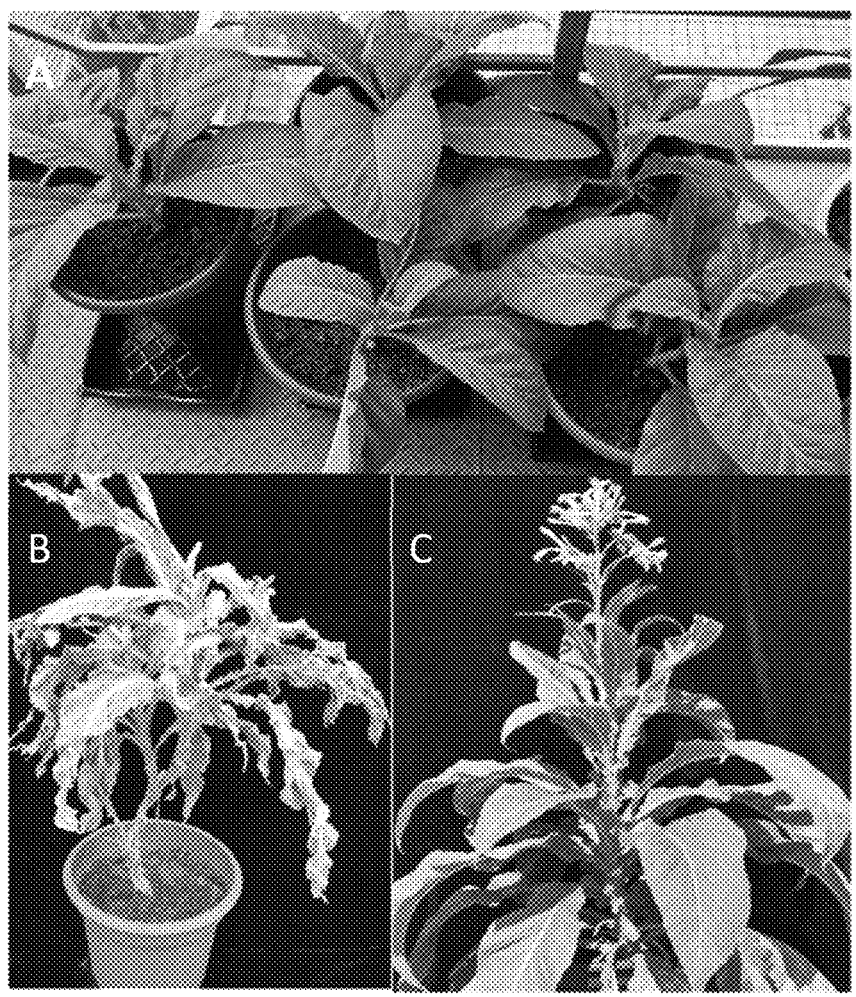
FIG. 6 shows the phenotype in the rosette stage and the adult stage. A, 5 plants, carrying RTSW resistance locus and breaking linkage drag, obtained from 160,000 tobacco screening. B, a typical TSWD resistance tobacco with linkage drag. C, the adult plant phenotype of plant No. 12; its main agronomic traits such as plant height, leaves and flowering period are the same as those of the elite cultivar 'K326'.

Example 9. Phenotype and TSWD Resistance Test of Self-Crossed Progenies of the Plant without linkage drag Whether the phenotype is completely restored to normal is the key point of the invention. Therefore, the phenotypes of the 5 resistant plants (No. 1, No. 4, No. 11, No. 12, and No. 17) selected in Example 8 were observed at seedling stage and adult stage. The observation results showed that the phenotypes of the 5 resistant plants at seedling stage and adult stage had no visible linkage drag, the morphology improved significantly, and the main agronomic traits such as plant height, leaves and flowering period were no significant different with the cultivar 'K326' (FIG. 6).

In order to detect whether the resistance introgressed segment still confers complete resistance to TSWV, self-crossed progenies of the plant No. 12 were inoculated with TSWV. The self-crossed progenies of the plant No. 12 were genotyped using molecular marker detection primers NaChr3_59MF/NaChr3_59MR. The plants that were positive or negative for the molecular marker were selected for rubbing inoculation with TSWV, and the symptoms were observed at two weeks postinoculation. Uninoculated systemic leaves at the top of the plants were collected for virus detection by ELISA. The method was as follows: (1) took 1-2 g TSWV source, put it in a mortar, added 5-10 mL of TSWV inoculation buffer (0.1M pH 7.0 phosphate buffer sterilized at 121° C. for 20 minutes; Within half an hour before inoculation, added 0.2 g sodium sulfite and 10 uL beta-mercaptoethanol per 100 mL phosphate buffer to make TSWV inoculation buffer and placed it on ice) and 2-3 g of carborundum (200-400 mesh), fully ground on ice until they were evenly mixed to obtain TSWV inoculum. For mechanical inoculation, carborundum (200-400 mesh) was first evenly sprinkled on the surface of a tobacco leaf to be inoculated at an amount of 0.1-0.2 g per leaf, then held the tobacco leaf to be inoculated with one hand, and rubbed the TSWV sap gently and evenly with the other hand from the base to the tip of the tobacco leaf to be inoculated; the dosage of TSWV inoculum was 50-100 ul per leaf; (2) after rubbing, rinsed the inoculated leaves with water, then cultivated the plants in the dark under a temperature of 22-25° C. with humidity of 60-80% for one day, and then moved the plants to growth chamber with a temperature of 22-25° C.,

TABLE 8

Marker detection results of recombination plants

| Plant | Marker name | | | | Resistance identification | Phenotype |
|---|---|---|---|---|---|---|
|  | NaChr3_59M | NaChr3_60M | NaChr3_62.6M | NaChr3_64.6M |  |  |
| 1# | Pos | Pos | Pos | Neg | Has HR | Normal |
| 4# | Pos | Pos | Neg | Neg | Has HR | Normal |
| 11# | Pos | Pos | Pos | Neg | Has HR | Normal |
| 12# | Pos | Neg | Neg | Neg | Has HR | Normal |
| 17# | Pos | Pos | Pos | Neg | Has HR | Normal |
| BC6F1-46# | Pos | Pos | Pos | Pos | Has HR | Deformed |
| *N. alata* | Pos | Pos | Pos | Pos | Has HR | Not defined |
| 'Polalta' | Pos | Pos | Pos | Pos | Has HR | Deformed |
| 'K326' | Neg | Neg | Neg | Neg | No HR | Normal |

Note:
"1#", "4#", "11#", "12#" and "17#" in the table represent "plant No. 1", "plant No. 4", "plant No. 11", "plant No. 12", "plant No. 17" respectively. "Pos" means positive, "Neg" means negative, and "HR" means hypersensitive reaction. "Has HR" means having TSWD resistance, and "No HR" means not having TSWD resistance.

a photoperiod of 14h day/10h night, and a humidity of 80%; (3) from the 9th day after inoculation, took fresh tobacco leaves every 7 days and used the double antibody sandwich ELISA method (Agdia, Cat. No. SRA 39300/0096) to detect TSWV and calculated the incidence of TSWD "a"; a total of four tests were performed. In order to reduce the error of human operation, for ELISA test, each sample was repeated three times. The operation steps of the double antibody sandwich ELISA method were carried out according to the instructions (Agdia, Cat. No. SRA 39300/0096).

Figure 7:
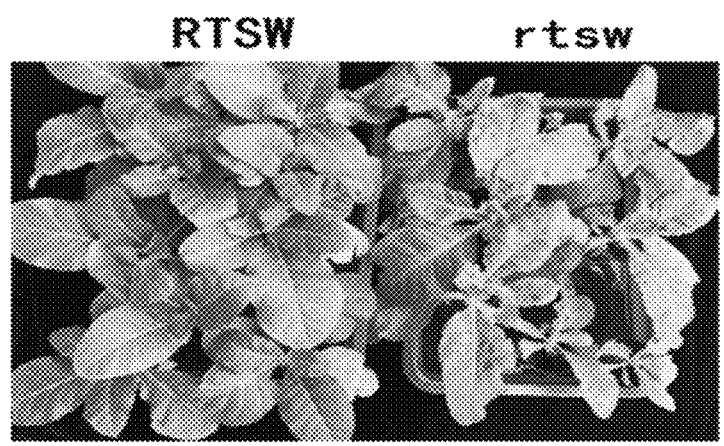
FIG. 7 shows virus inoculation test of self-crossed progenies of plant No. 12. Self-crossed progenies of plant No. 12 were genotyped using amplification primers NaChr3_59MF/NaChr3_59MR for NaChr3_59M molecular marker. Plants that comprise the molecular marker (marked as RTSW in the figure) and those that do not comprise the molecular marker (marked as rtsw in the figure) were selected and inoculated with Tomato spotted wilt virus (TSWV) by rubbing, and TSWV symptoms were observed at two weeks postinoculation. It was found that the plants carrying the resistance introgressed segment were completely resistant to the disease, and the plants without the resistance introgressed segment were 100% diseased.

The total number of infected plants was the total number of positive plants in the four tests. Incidence "a"=(number of susceptible plants of the variety/total number of plants of the variety)×100%. The results of genotyping, symptom observation after inoculation and ELISA test showed that 12 plants carrying the resistance introgressed segment (detected as positive for NaChr3_59M marker) were completely resistant to the disease, while 12 plants without the resistance introgressed segment (detected as negative for NaChr3_59M marker) were 100% susceptible (FIG. 7).

Example 10. Analysis of Agronomic Traits of Materials without Linkage Drag

The plant No. 12 carrying the shortest RTSW introgressed segment was self-crossed, and the self-crossed progenies were genotyped using molecular marker detection primers NaChr3_59MF/NaChr3_59MR. 1000 homozygous plants (genotype RTSW/RTSW) of F3 generation were growth in the field in 2021 (indicated as K326-RTSW in Table 9), and the cultivar 1(326' was growth as a control. There was no difference between all K326-RTSW plants (carrying the shortest RTSW introgressed segment) and the control plants (cultivar 'K326') in terms of germination rate, survival rate, and field growth at the seedling stage. At the vegetative and reproductive stage, 10 plants were randomly selected to measure plant height, stem circumference, leaf number, leaf length, leaf width and other performances to test the agronomic traits of K326-RTSW (Table 9).

TABLE 9

| Analysis of agronomic traits | | | | | |
|---|---|---|---|---|---|
| | Natural plant height at full flowering stage (cm) | Natural plant height at green fruit stage (cm) | Topping plant height (cm) | Total number of leaves at full flowering stage (blade) | Stem circumference at full flowering stage (cm) |
| K326-RTSW | 133.45 ± 12.08 | 153.9 ± 13.46 | 134.86 ± 10.35 | 26.8 ± 2.48 | 10 ± 0.77 |
| K326 | 139.2 ± 18.61 | 159.2 ± 18.93 | 141.95 ± 8.08 | 26.4 ± 1.28 | 10.23 ± 0.83 |
| p-value | 0.4397 | 0.1022 | 0.1741 | 0.3104 | 0.3329 |
| | Stem circumference at green fruit stage (cm) | Midstalk leaf length at full flowering stage (cm) | Midstalk leaf width at full flowering stage (cm) | Midstalk leaf length at green fruit stage (cm) | Midstalk leaf width at green fruit stage (cm) |
| K326-RTSW | 10.69 ± 0.79 | 71.96 ± 3.46 | 32.44 ± 2.89 | 73.54 ± 4.52 | 32.41 ± 3.06 |
| K326 | 10.51 ± 0.9 | 68.83 ± 4.74 | 34.5 ± 3 | 70.26 ± 5.62 | 32.54 ± 2.66 |
| p-value | 0.2193 | 0.0918 | 0.2003 | 0.5050 | 0.7599 |

From the table, we can find that the linkage drag has been completely segregated from the short RTSW introgressed segment. The obtained K326-RTSW variety carrying the short RTSW introgressed segment had no significant difference from the elite cultivar 'K326' in terms of plant height, stem circumference, number of leaves, leaf length, leaf width and other agronomic traits.

SEQUENCE LISTING

The patent contains a lengthy sequence listing. A copy of the sequence listing is available in electronic form from the USPTO web site (https://seqdata.uspto.gov/?pageRequest=docDetail&DocID=US12144310B2). An electronic copy of the sequence listing will also be available from the USPTO upon request and payment of the fee set forth in 37 CFR 1.19(b)(3).

The invention claimed is:

1. A non-naturally occurring tobacco plant or germplasm with resistance to tobacco spotted wilt disease (TSWD) and without linkage drag, which is obtained by hybridization using tobacco variety 'Polalta' as TSWD resistance donor parent and a TSWD susceptible tobacco variety as recipient parent and recurrent parent, wherein said non-naturally occurring tobacco plant or germplasm comprises NaChr3_59M marker as set forth in SEQ ID NO: 5, and wherein said non-naturally occurring tobacco plant or germplasm does not comprise NaChr3_44.2M marker as set forth in SEQ ID NO: 1, NaChr3_54M marker as set forth in SEQ ID NO: 2, NaChr3_57M marker as set forth in SEQ ID NO: 3, NaChr3 58M marker as set forth in SEQ ID NO: 4, NaChr3_64.6M marker as set forth in SEQ ID NO: 8, NaChr4_2M marker as set forth in SEQ ID NO: 10 and NaChr4 8M marker as set forth in SEQ ID NO: 11.

2. The non-naturally occurring tobacco plant or germplasm according to claim 1, wherein the non-naturally occurring tobacco plant or germplasm further does not comprise NaChr3_62.6M marker as set forth in SEQ ID NO: 7.

3. The non-naturally occurring tobacco plant or germplasm according to claim 1, wherein the non-naturally occurring tobacco plant or germplasm is selected from the group consisting of Burley tobacco, Dark tobacco, Flue-cured tobacco, Maryland tobacco, Oriental tobacco and Cigar tobacco.

4. A method for screening a tobacco plant or germplasm with resistance to tobacco spotted wilt disease (TSWD) and without linkage drag, the method comprising:
(a) isolating nucleic acids from tobacco plants or germplasms that are obtained by hybridization using tobacco variety 'Polalta' as TSWD resistance donor parent and a TSWD susceptible tobacco variety as recipient parent and recurrent parent;
(b) detecting a TSWD resistance marker, a first linkage drag locus marker and a second linkage drag locus marker in the isolated nucleic acids, wherein the TSWD resistance marker comprises NaChr3_59M marker as set forth in SEQ ID NO: 5, wherein the first linkage drag locus marker comprises NaChr4_2M marker as set forth in SEQ ID NO: 10 and NaChr4_8M marker as set forth in SEQ ID NO: 11, wherein the second linkage drag locus marker comprises NaChr3_44.2M marker as set forth in SEQ ID NO: 1, NaChr3_54M marker as set forth in SEQ ID NO: 2, NaChr3_ 57M marker as set forth in SEQ ID NO: 3, NaChr3_58M marker as set forth in SEQ ID NO: 4, and NaChr3_64.6M marker as set forth in SEQ ID NO: 8; and
(c) selecting a tobacco plant or germplasm that comprises the TSWD resistance marker and does not comprise the first linkage drag locus marker and the second linkage drag locus marker, and wherein said selected a tobacco plant or germplasm is non-naturally occurring.

5. The method according to claim 4, wherein the second linkage drag locus marker further comprises NaChr3_62.6M marker as set forth in SEQ ID NO: 7.

6. The method according to claim 4, wherein the detection includes polymerase chain reaction er and nucleic acid sequencing.

7. A method for breeding a tobacco plant or germplasm with resistance to tobacco spotted wilt disease (TSWD) and without linkage drag, the method comprising:
(a) crossing a first tobacco plant or germplasm thereof with a second tobacco plant or germplasm thereof to produce a progeny tobacco plant or germplasm thereof, wherein the first tobacco plant or germplasm thereof comprises a TSWD resistance marker and does not comprise a first linkage drag locus marker and a second linkage drag locus marker wherein the TSWD resistance marker comprises NaChr3_59M marker as set forth in SEQ ID NO:. 5, wherein the first linkage drag locus marker comprises NaChr4_2M marker as set forth in SEQ ID NO: 10 and NaChr4_8M marker as set forth in SEQ ID NO: 11, wherein the second linkage drag locus marker comprises NaChr3_44.2M marker as set forth in SEQ ID NO: 1, NaChr3_54M marker as set forth in SEQ ID NO: 2, NaChr3_57M marker as set forth in SEQ ID NO: 3, NaChr3 58M marker as set forth in SEQ ID NO: 4, and NaChr3_64.6M marker as set forth in SEQ ID NO: 8, and wherein the first tobacco plant or germplasm thereof is obtained by hybridization using tobacco variety 'Polalta' as TSWD resistance donor parent and a TSWD susceptible tobacco variety as recipient parent and recurrent parent;
(b) isolating nucleic acids from the progeny tobacco plant or germplasm thereof; and
(c) detecting the TSWD resistance marker, the first linkage drag locus marker, and the second linkage drag locus marker in the isolated nucleic acids, thereby producing a progeny tobacco plant or germplasm that comprises the TSWD resistance marker and does not comprise the first linkage drag locus marker and the second linkage drag locus marker, and wherein said produced progeny tobacco plant or germplasm of step (c) is non-naturally occurring.

8. The method according to claim 7, wherein the second linkage drag locus marker further comprises NaChr3_62.6M marker as set forth in SEQ ID NO: 7.

9. The method according to claim 7, wherein the detection includes polymerase chain reaction and nucleic acid sequencing.

10. The method according to claim 7, wherein the first tobacco plant or germplasm thereof and the second tobacco plant or germplasm thereof are selected from the group consisting of Burley tobacco, Dark tobacco, Flue-cured tobacco, Maryland tobacco, Oriental tobacco and Cigar tobacco.

* * * * *